(12) United States Patent
Kwon et al.

(10) Patent No.: US 11,591,347 B2
(45) Date of Patent: Feb. 28, 2023

(54) COMPOUNDS AND FILMS AND PHOTOELECTRIC DIODES AND ORGANIC SENSORS AND ELECTRONIC DEVICES

(71) Applicant: Samsung Electronics Co., Ltd., Suwon-si (KR)

(72) Inventors: Ohkyu Kwon, Seoul (KR); Hyesung Choi, Seoul (KR); Dong-Seok Leem, Seongnam-si (KR); Hwang Suk Kim, Suwon-si (KR); Bum Woo Park, Hwaseong-si (KR); Kwang Hee Lee, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/530,303

(22) Filed: Aug. 2, 2019

(65) Prior Publication Data

US 2020/0157120 A1    May 21, 2020

(30) Foreign Application Priority Data

Nov. 15, 2018 (KR) .................. 10-2018-0140838

(51) Int. Cl.
  *C07D 519/00* (2006.01)
  *H01L 51/00* (2006.01)
  *C09K 11/06* (2006.01)

(52) U.S. Cl.
  CPC ............ *C07D 519/00* (2013.01); *C09K 11/06* (2013.01); *H01L 51/0059* (2013.01); *H01L 51/0065* (2013.01); *H01L 51/0068* (2013.01); *H01L 51/0072* (2013.01); *H01L 51/0073* (2013.01); *H01L 51/0074* (2013.01)

(58) Field of Classification Search
  None
  See application file for complete search history.

(56) References Cited

U.S. PATENT DOCUMENTS

2018/0219160 A1    8/2018  Tokito et al.

FOREIGN PATENT DOCUMENTS

| CN | 103936653 A   | 7/2014  |
|----|---------------|---------|
| CN | 107188899 A   | 9/2017  |
| JP | 2017025039 A  | 2/2017  |
| JP | 2018111673 A  | 7/2018  |
| JP | 2018111675 A  | 7/2018  |
| JP | 2018129510 A  | 8/2018  |
| KR | 20150086737 A | 7/2015  |
| KR | 101569854 B1  | 12/2015 |
| WO | WO-2016024567 A1 | 2/2016 |
| WO | WO-2018015320 A1 | 1/2018 |

OTHER PUBLICATIONS

Machine generated English Translation of Japanese Patent Application Publication No. 2018-111675 published on Jul. 19, 2018.*
Thomas, A. et al. "Substituents Destabilize the Molecule by Increasing Biradicaloid Character and Stabilize by Intramolecular Charge Transfer in the Derivatives of Benzobis(thiadiazole) and Thiadiazolothienopyrazine: A Cumputional Study" ChemPhyschem 2011, 12, 3458-3466.
Tian, M. et al. "Search for Squaraine Derivatives That Can be Sublimed without Thermal Decomposition" J. Phys. Chem. B 2002, 106, 4370-4376.
Qian, G. et al. "Simple and Efficient Near-Infrared Organic Chromophores for Light-Emitting Diodes with Single Electroluminescent Emission above 1000 nm" Adv. Mater. 2009, 21, 111-116.
Kono, T. et al. "Dithienylbenzobis(thiadiazole) based organic semiconductors with low LUMO levels and narrow energy gaps" Chem. Commun., 2010, 46, 3265-3267.
Kawabata, K. et al. "Very Small Bandgap $\pi$—Conjugated Polymers with Extended Thienoquinoids" JACS, 2016, 138, 7725-7732.
Lim, B. et al. "Ternary Bulk Heterojunction Solar Cells: Addition of Soluble NIR dyes for Photocurrent Generation beyond 800 nm" ACS Appl. Mater. Interfaces, 2014, 6, 6905-6913.

* cited by examiner

*Primary Examiner* — Po-Chih Chen
(74) *Attorney, Agent, or Firm* — Harness, Dickey & Pierce, P.L.C.

(57) ABSTRACT

A composition may include a compound, a film may include the composition, an organic layer of an organic sensor and/or photoelectric diode may include the compound, and the film, organic sensor, and/or photoelectric diode may be included in an electronic device.

25 Claims, 14 Drawing Sheets

COMPOUNDS AND FILMS AND PHOTOELECTRIC DIODES AND ORGANIC SENSORS AND ELECTRONIC DEVICES

CROSS-REFERENCE TO RELATED APPLICATION

This application claims priority to and the benefit of Korean Patent Application No. 10-2018-0140838 filed in the Korean Intellectual Property Office on Nov. 15, 2018, the entire contents of which are incorporated herein by reference.

BACKGROUND

1. Field

Compounds, film, photoelectric diodes, organic sensors, and electronic devices are disclosed.

2. Description of the Related Art

Imaging devices are used in digital cameras, camcorders, etc., to capture an image and to store the captured image as an electrical signal, and imaging devices include a sensor that may separate incident light into separate components defined by separate wavelength regions and convert each separate component to an electrical signal. Accordingly, it will be understood that the sensor may detect the incident light in the separate wavelength regions.

In recent years, photoelectric diodes configured to detect light in a near infra-red wavelength region have been studied for improving sensitivity of a sensor in a low-illuminance environment or for use as a biometric device.

SUMMARY

Some example embodiments provide a compound having good light absorption characteristics in a near infra-red region.

Some example embodiments provide a film including the compound.

Some example embodiments provide a photoelectric diode including the compound.

Some example embodiments provide an organic sensor including the compound or the photoelectric diode.

Some example embodiments provide an electronic device including the photoelectric diode or the organic sensor.

According to some example embodiments, a composition may include a compound represented by Chemical Formula.

[Chemical Formula 1]

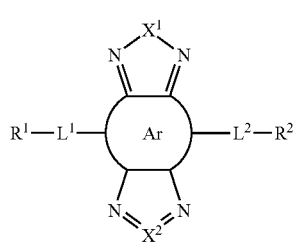

In Chemical Formula 1,
$X^1$ and $X^2$ are independently O, S, Se, Te, SO, $SO_2$, or $NR^a$, Ar is a substituted or unsubstituted C6 to C20 aromatic ring, $L^1$ and $L^2$ are independently a single bond, a substituted or unsubstituted C6 to C20 arylene group, a substituted or unsubstituted divalent C3 to C20 heterocyclic group, a fused ring of a substituted or unsubstituted C6 to C20 arylene group and a substituted or unsubstituted divalent C3 to C20 heterocyclic group, or any combination thereof, $L^1$, $L^2$, or both $L^1$ and $L^2$ includes the fused ring of the substituted or unsubstituted C6 to C20 arylene group and the substituted or unsubstituted divalent C3 to C20 heterocyclic group, and $R^1$, $R^2$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^1$, $R^2$, or both $R^1$ and $R^2$ is a substituted or unsubstituted amine group represented by $NR^bR^c$, wherein each $R^b$ is the same or different, each $R^c$ is the same or different, and $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, and $R^b$ and $R^c$ are independently present or are linked with each other to form a ring.

$L^1$, $L^2$, or both $L^1$ and $L^2$ may include a fused ring of a substituted or unsubstituted phenylene group and a divalent substituted or unsubstituted C3 to C30 heterocyclic group including at least one of O, S, Se, Te, N, and Si.

$L^1$, $L^2$, or both Land $L^2$ may include one of substituted or unsubstituted groups of Group 1.

[Group 1]

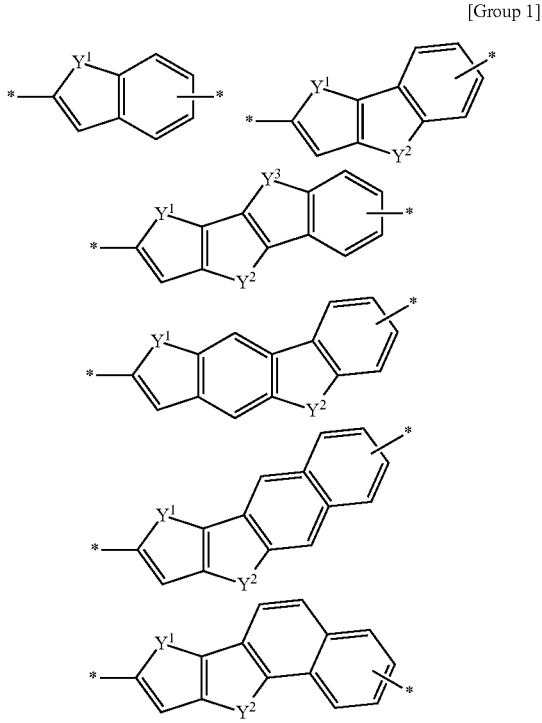

-continued

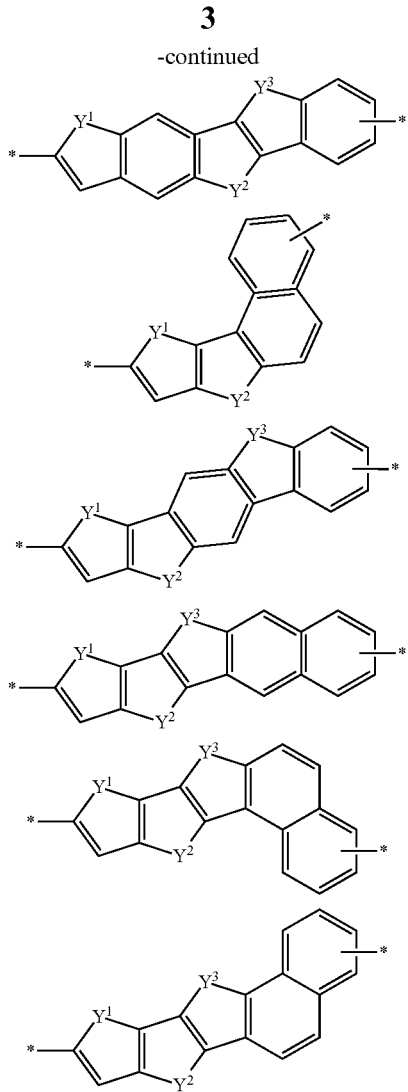

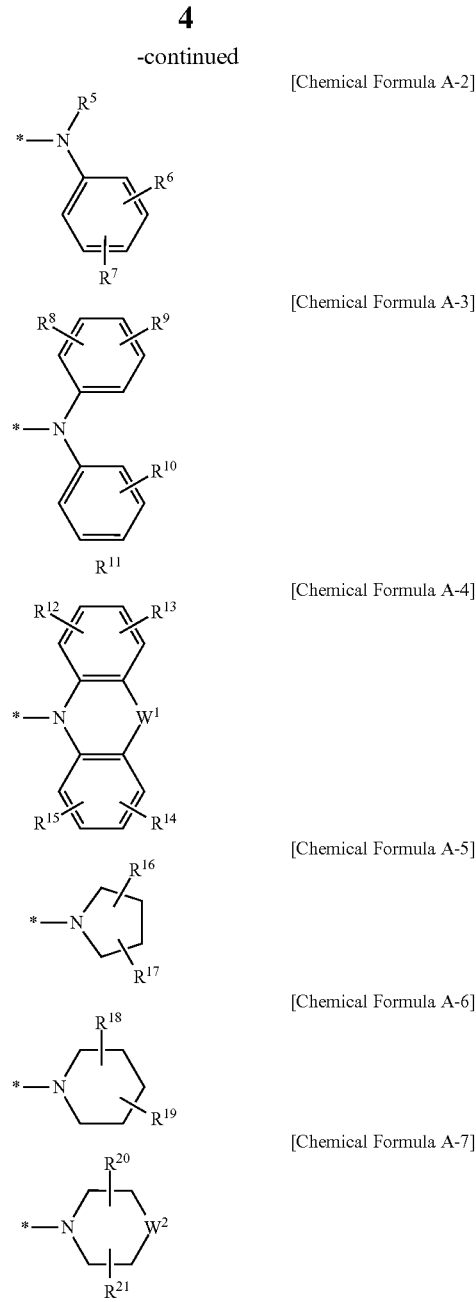

In Group 1, $Y^1$, $Y^2$, and $Y^3$ are independently O, S, Se, Te, $NR^d$, or $SiR^eR^f$, wherein $R^d$ to $R^f$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^e$ and $R^f$ are independently present or are linked with each other to form a ring, and

* is a linking point with Chemical Formula 1.

$R^1$, $R^2$, or both $R^1$ and $R^2$ may be represented by one of Chemical Formulae A-1 to A-7.

[Chemical Formula A-1]

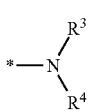

In Chemical Formulae A-1 to A-7, $W^1$ is a single bond, O, S, Se, Te, $CR^gR^h$, or $SiR^iR^j$, $W^2$ is O, S, Se, Te, $CR^kR^l$, or $SiR^mR^n$, $R^3$ to $R^{21}$ and $R^g$ to $R^n$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^3$ and $R^4$ are independently present or are linked with each other to form a ring, $R^6$ and $R^7$ are independently present or are linked with each other to form a ring, $R^8$ and $R^9$ are independently present or are linked with each other to form a ring, $R^{19}$ and $R^{11}$ are independently present or are linked with each other to form a ring, $R^{12}$ and $R^{13}$ are independently present or are linked with each other to form a ring, $R^{14}$ and $R^{15}$ are independently present or are linked with each other to form a ring, $R^{16}$ and $R^{17}$ are independently present or are linked with each other to form a ring, $R^{18}$ and $R^{19}$ are independently present or are linked with each other to form a ring, $R^{29}$ and $R^{21}$ are independently present or are linked with each other to form a ring, $R^g$ and $R^h$ are independently present or are linked with each other to form a ring, $R^i$ and $R^j$ are independently present or are linked with each other to form a ring, $R^k$ and $R^l$ are independently present or are linked with each other to form a ring, $R^m$ and $R^n$ are independently present or are linked with each other to form a ring, and is a linking point with Chemical Formula 1.

The compound may be represented by Chemical Formula 1A.

[Chemical Formula 1A]

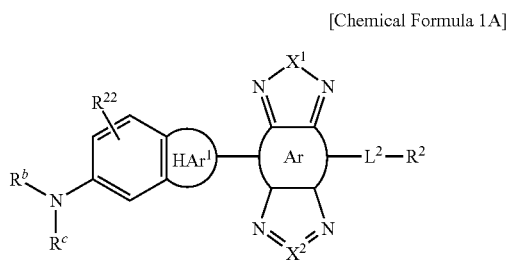

In Chemical Formula 1A, $X^1$ and $X^2$ are independently O, S, Se, Te, SO, SO$_2$, or NR$^a$, Ar is a substituted or unsubstituted C6 to C20 aromatic ring, HAr$^1$ is a heterocyclic group including a substituted or unsubstituted thiophenylene group, a substituted or unsubstituted furanylene group, a substituted or unsubstituted selenophenylene group, a substituted or unsubstituted tellurophenylene group, a substituted or unsubstituted pyrrolylene group, or any combination thereof, $L^2$ is a single bond, a substituted or unsubstituted C6 to C20 arylene group, a substituted or unsubstituted divalent C3 to C20 heterocyclic group, a fused ring of a substituted or unsubstituted C6 to C20 arylene group and a substituted or unsubstituted divalent C3 to C20 heterocyclic group, or any combination thereof, $R^2$, $R^{22}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, and $R^b$ and $R^c$ are independently present or are linked with each other to form a ring.

The compound may be represented by Chemical Formula 1B.

[Chemical Formula 1B]

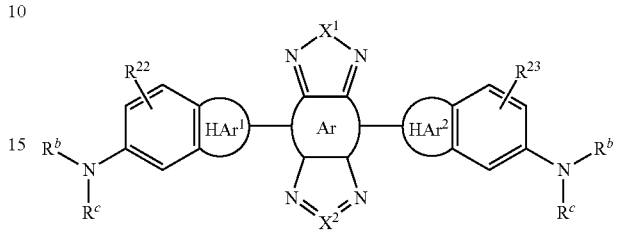

In Chemical Formula 1B, $X^1$ and $X^2$ are independently O, S, Se, Te, SO, SO$_2$, or NR$^a$, Ar is a substituted or unsubstituted C6 to C20 aromatic ring, HAr$^1$ and HAr$^2$ are independently a heterocyclic group including a substituted or unsubstituted thiophenylene group, a substituted or unsubstituted furanylene group, a substituted or unsubstituted selenophenylene group, a substituted or unsubstituted tellurophenylene group, a substituted or unsubstituted pyrrolylene group, or any combination thereof, $R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, each $R^b$ is the same or different, each $R^c$ is the same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, and $R^b$ and $R^c$ are independently present or are linked with each other to form a ring.

The compound may be represented by Chemical Formula 1C.

[Chemical Formula 1C]

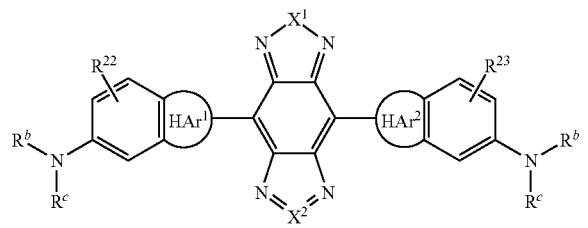

In Chemical Formula 1C, $X^1$ and $X^2$ are independently O, S, Se, Te, SO, $SO_2$, or $NR^a$, $HAr^1$ and $HAr^2$ are independently a heterocyclic group including a substituted or unsubstituted thiophenylene group, a substituted or unsubstituted furanylene group, a substituted or unsubstituted selenophenylene group, a substituted or unsubstituted tellurophenylene group, a substituted or unsubstituted pyrrolylene group, or any combination thereof, $R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, each $R^b$ is the same or different, each $R^c$ is the same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, and $R^b$ and $R^c$ are independently present or are linked with each other to form a ring.

A peak absorption wavelength of the compound may belong to a wavelength region of about 750 nm to about 3000 nm.

According to some example embodiments, a film including the compound is provided.

According to some example embodiments, a photoelectric diode includes a first electrode and a second electrode facing each other and an organic layer disposed between the first electrode and the second electrode, wherein the organic layer includes a compound represented by Chemical Formula 1.

A peak absorption wavelength of the organic layer may belong to a wavelength region of about 750 nm to about 3000 nm.

According to some example embodiments, an organic sensor including the photoelectric diode is provided.

According to some example embodiments, an electronic device including the photoelectric diode or the organic sensor is provided.

According to some example embodiments, an organic sensor may include a semiconductor substrate and a photoelectric device on the semiconductor substrate. The photoelectric device may be configured to absorb and convert a first wavelength spectrum of incident light into electric signals. The photoelectric device may include a compound represented by Chemical Formula 1,

[Chemical Formula 1]

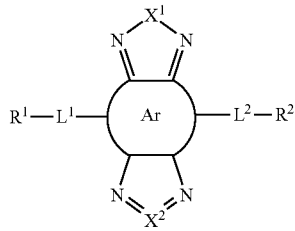

wherein, in Chemical Formula 1, $X^1$ and $X^2$ are independently O, S, Se, Te, SO, $SO_2$, or $NR^a$, Ar is a substituted or unsubstituted C6 to C20 aromatic ring, $L^1$ and $L^2$ are independently a single bond, a substituted or unsubstituted C6 to C20 arylene group, a substituted or unsubstituted divalent C3 to C20 heterocyclic group, a fused ring of a substituted or unsubstituted C6 to C20 arylene group and a substituted or unsubstituted divalent C3 to C20 heterocyclic group, or any combination thereof, $L^1$, $L^2$, or both $L^1$ and $L^2$ includes the fused ring of the substituted or unsubstituted C6 to C20 arylene group and the substituted or unsubstituted divalent C3 to C20 heterocyclic group, and $R^1$, $R^2$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, and $R^1$, $R^2$, or both $R^1$ and $R^2$ is a substituted or unsubstituted amine group represented by $NR^bR^c$, wherein each $R^b$ is same or different, each $R^c$ is same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, $R^b$ and $R^c$ are independently present or are linked with each other to form a ring.

The organic sensor may further include a plurality of photoelectric devices on the semiconductor substrate. Each photoelectric device of the plurality of photoelectric devices may be configured to absorb and convert a different wavelength spectra of incident light into electric signals. The plurality of photoelectric devices may include the photoelectric device.

The plurality of photoelectric devices may be stacked vertically on the semiconductor substrate, such that the plurality of photoelectric devices overlap each other in a direction extending perpendicular to a top surface of the semiconductor substrate.

One photoelectric device of the plurality of photoelectric devices may overlap with a limited portion of another photoelectric device of the plurality of photoelectric devices in the direction extending perpendicular to the top surface of the semiconductor substrate.

The plurality of photoelectric devices may be arranged horizontally on the semiconductor substrate, such that the plurality of photoelectric devices overlap each other in a direction extending parallel to a top surface of the semiconductor substrate.

The first wavelength spectrum of incident light may include an infrared or near-infrared wavelength spectrum of incident light.

The organic sensor may further include a photo-sensing device integrated in the semiconductor substrate, the photo-sensing device configured to convert a second wavelength spectrum of incident light into electric signals.

The organic sensor may further include a color filter configured to selectively transmit a particular wavelength spectrum of incident light to the photo-sensing device, the particular wavelength spectrum of incident light including at least the second wavelength spectrum of incident light, such that the photo-sensing device is configured to absorb the second wavelength spectrum of incident light.

The photoelectric device may be between the color filter and the photo-sensing device.

The photo-sensing device may be between the color filter and the photoelectric device.

An electronic device may include the organic sensor of claim 21.

The compound exhibits good light absorption characteristics in a near infra-red region and thus may be effectively used for a photoelectric diode and/or an organic sensor

DETAILED DESCRIPTION

Figure 1:
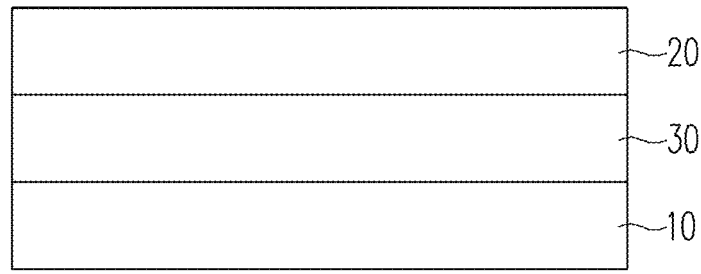
FIG. 1 is a cross-sectional view of a photoelectric diode according to some example embodiments.

Hereinafter, example embodiments of the present disclosure will be described in detail so that a person skilled in the art would understand the same. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

When a definition is not otherwise provided, "substituted" may refer to replacement of hydrogen of a compound by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heterocyclic group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and any combination thereof.

As used herein, when a definition is not otherwise provided, "hetero" may refer to inclusion of one to four heteroatoms selected from N, O, S, Se, Te, Si, and P.

As used herein, when a definition is not otherwise provided, "aromatic ring" may refer to a functional group in which all atoms in the cyclic functional group have a p-orbital, and wherein these p-orbitals are conjugated.

As used herein, when a definition is not otherwise provided, "aryl group" may refer to a group including at least one hydrocarbon aromatic moiety, and may include a group in which all elements of the hydrocarbon aromatic moiety have p-orbitals which form conjugation, for example a phenyl group, a naphthyl group, and the like; a group in which two or more hydrocarbon aromatic moieties may be linked by a sigma bond, for example a biphenyl group, a terphenyl group, a quarterphenyl group, and the like; and a group in which two or more hydrocarbon aromatic moieties are fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heterocyclic group" may be a generic concept of a "heteroaryl group" and may refer to a cyclic group including at least one heteroatom selected from N, O, S, Se, Te, P, and Si instead of carbon (C) in the cyclic group. When the heterocyclic group is a fused ring, at least one of rings of the heterocyclic group may have a heteroatom or each ring may have a heteroatom.

As used herein, when a definition is not otherwise provided, "ring" may refer to an aromatic ring, a non-aromatic ring, a heteroaromatic ring, a hetero non-aromatic ring, a fused ring thereof, and/or any combination thereof.

Hereinafter, a composition including a compound according to some example embodiments is described.

A composition may include compound according to some example embodiments, and the compound may be represented by Chemical Formula 1.

[Chemical Formula 1]

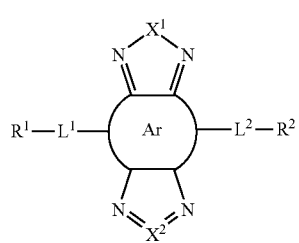

In Chemical Formula 1, $X^1$ and $X^2$ are independently O, S, Se, Te, SO, $SO_2$, or $NR^a$, Ar is a substituted or unsubstituted C6 to C20 aromatic ring, $L^1$ and $L^2$ are independently a single bond, a substituted or unsubstituted C6 to C20 arylene group, a substituted or unsubstituted divalent C3 to C20 heterocyclic group, a fused ring of a substituted or unsubstituted C6 to C20 arylene group and a substituted or unsubstituted divalent C3 to C20 heterocyclic group, or any combination thereof, $L^1$, $L^2$, or both $L^1$ and $L^2$ includes the fused ring of the substituted or unsubstituted C6 to C20 arylene group and the substituted or unsubstituted divalent C3 to C20 heterocyclic group, and $R^1$, $R^2$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^1$, $R^2$, or both $R^1$ and $R^2$ is a substituted or unsubstituted amine group represented by $NR^bR^c$, wherein each $R^b$ is the same or different, each $R^c$ is the same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, $R^b$ and $R^c$ are independently present or are linked with each other to form a ring.

The compound includes a core of a conjugation structure having an electron accepting property which is bound to a substituted or unsubstituted amine group having an electron donating property by a fused ring, and thereby effectively absorbs light in a near infra-red wavelength region. The compound has light-absorbing characteristics and simultaneously good electrical characteristics.

A peak absorption wavelength (Amax) of the compound may be for example greater than or equal to about 700 nm, greater than or equal to about 720 nm, greater than or equal to about 730 nm, greater than or equal to about 750 nm, greater than or equal to about 780 nm, greater than or equal to about 790 nm, greater than or equal to about 800 nm, greater than or equal to about 810 nm, greater than or equal to about 820 nm, greater than or equal to about 830 nm, greater than or equal to about 840 nm, greater than or equal to about 850 nm, greater than or equal to about 870 nm, greater than or equal to about 890 nm, greater than or equal to about 900 nm, or greater than or equal to about 910 nm. The peak absorption wavelength of the compound may for example include and/or be included within a wavelength region ("wavelength spectrum") of about 700 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, about 830 nm to about 2000 nm, about 850 nm to about 1900 nm, about 870 nm to about 1800 nm, about 900 nm to about 1600 nm, or about 910 nm to about 1500 nm.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In some example embodiments, Ar may be a substituted or unsubstituted benzene, a substituted or unsubstituted naphthalene or a substituted or unsubstituted anthracene.

In some example embodiments, $L^1$, $L^2$, or both $L^1$ and $L^2$ may include a fused ring of a substituted or unsubstituted phenylene group or a substituted or unsubstituted naphthylene group and a divalent substituted or unsubstituted C3 to C30 heterocyclic group including O, S, Se, Te, N, Si, or any combination thereof. In some example embodiments, $L^1$, $L^2$, or both $L^1$ and $L^2$ may be a fused ring of a substituted or unsubstituted phenylene group or a substituted or unsubstituted naphthylene group, and a substituted or unsubstituted thiophenylene group, a substituted or unsubstituted benzothiophenylene group, a substituted or unsubstituted dibenzothiophenylene group, a substituted or unsubstituted furanylene group, a substituted or unsubstituted benzofuranylene group, a substituted or unsubstituted dibenzofuranylene group, a substituted or unsubstituted selenophenylene group, a substituted or unsubstituted benzoselenophenylene group, a substituted or unsubstituted dibenzoselenophenylene group, a substituted or unsubstituted tellurophenylene group, a substituted or unsubstituted benzotellurophenylene group, a substituted or unsubstituted dibenzotellurophenylene group, a substituted or unsubstituted pyrrolylene group, a substituted or unsubstituted benzopyrrolylene group, a substituted or unsubstituted dibenzopyrrolylene group, or any combination thereof.

In some example embodiments, $L^1$, $L^2$, or both $L^1$ and $L^2$ may include one of substituted or unsubstituted groups of Group 1 but is not limited thereto.

[Group 1]

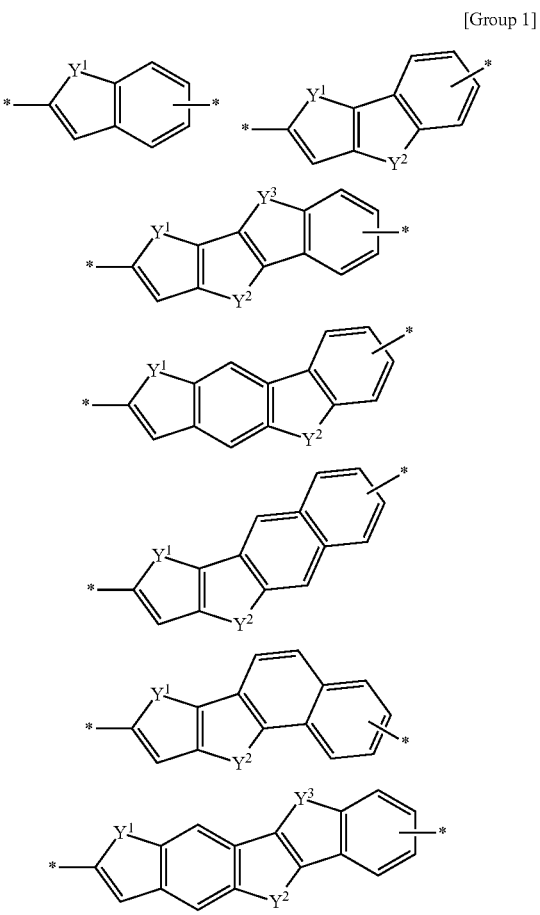

-continued

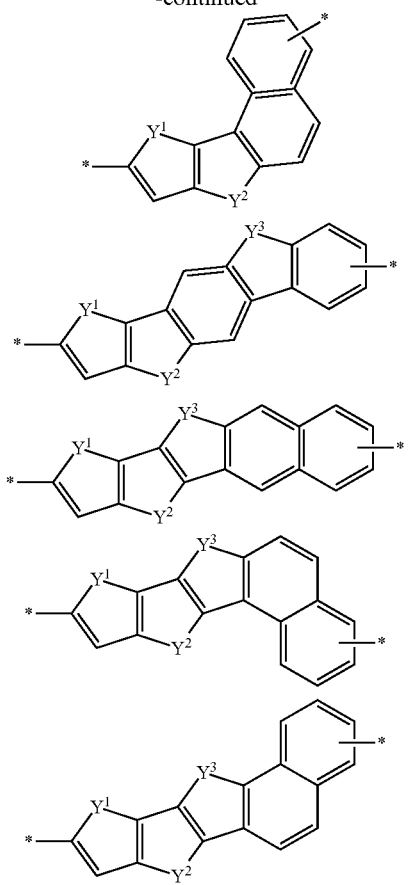

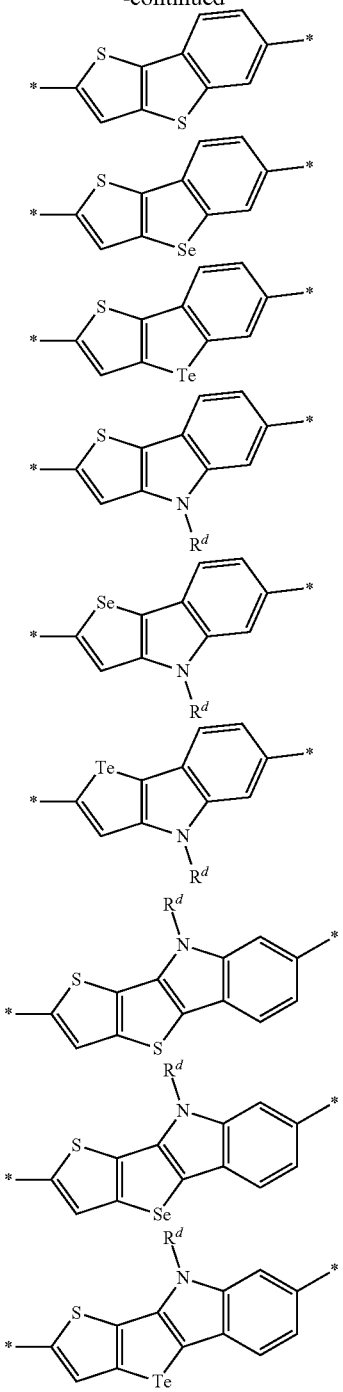

In Group 1, $Y^1$, $Y^2$, and $Y^3$ are independently O, S, Se, Te, $NR^d$ or $SiR^eR^f$, wherein $R^d$ to $R^f$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^e$ and $R^f$ are independently present or are linked with each other to form a ring, and is a linking point with Chemical Formula 1.

In some example embodiments, $L^1$, $L^2$, or both $L^1$ and $L^2$ may include one of substituted or unsubstituted groups of Group 1A but is not limited thereto.

[Group 1A]

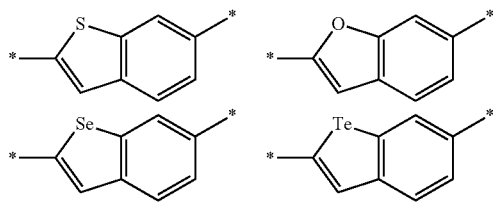

In Group 1A, $R^d$ is the same as described above.

In some example embodiments, $L^1$ and $L^2$ may independently include a fused ring of a substituted or unsubstituted phenylene group or a substituted or unsubstituted naphthylene group and a divalent substituted or unsubstituted C3 to C30 heterocyclic group including O, S, Se, Te, N, Si, or any combination thereof.

In some example embodiments, $L^1$ and $L^2$ may independently include one of substituted or unsubstituted groups of Group 1.

In some example embodiments, $L^1$ and $L^2$ may independently include one of substituted or unsubstituted groups of Group 1A.

In some example embodiments, $L^1$ and $L^2$ may be the same

In some example embodiments, $L^1$ and $L^2$ may be different.

In some example embodiments, $R^1$, $R^2$, or both $R^1$ and $R^2$ may be represented by one Chemical Formula of Chemical Formulae A-1 to A-7.

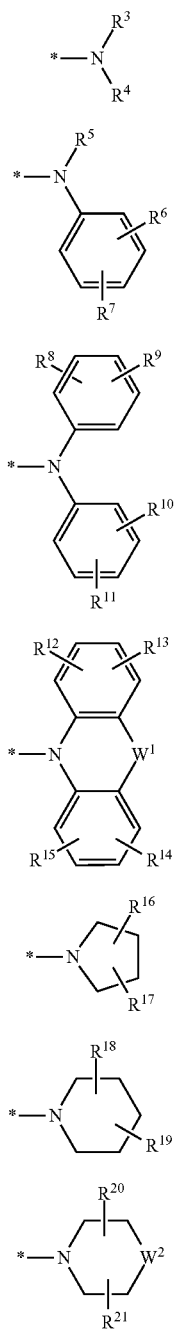

[Chemical Formula A-1]

[Chemical Formula A-2]

[Chemical Formula A-3]

[Chemical Formula A-4]

[Chemical Formula A-5]

[Chemical Formula A-6]

[Chemical Formula A-7]

In Chemical Formulae A-1 to A-7, $W^1$ is a single bond, O, S, Se, Te, $CR^gR^h$, or $SiR^iR^j$, $W^2$ is O, S, Se, Te, $CR^kR^l$, or $SiR^mR^n$, $R^3$ to $R^{21}$ and $R^g$ to $R^n$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^3$ and $R^4$ are independently present or are linked with each other to form a ring, $R^6$ and $R^7$ are independently present or are linked with each other to form a ring, $R^8$ and $R^9$ are independently present or are linked with each other to form a ring, $R^{10}$ and $R^{11}$ are independently present or are linked with each other to form a ring, $R^{12}$ and $R^{13}$ are independently present or are linked with each other to form a ring, $R^{14}$ and $R^{15}$ are independently present or are linked with each other to form a ring, $R^{16}$ and $R^{17}$ are independently present or are linked with each other to form a ring, $R^{18}$ and $R^{19}$ are independently present or are linked with each other to form a ring, $R^{20}$ and $R^{21}$ are independently present or are linked with each other to form a ring, $R^g$ and $R^h$ are independently present or are linked with each other to form a ring, $R^i$ and $R^j$ are independently present or are linked with each other to form a ring, $R^k$ and $R^l$ are independently present or are linked with each other to form a ring, $R^m$ and $R^n$ are independently present or are linked with each other to form a ring, and \* is a linking point with Chemical Formula 1.

In some example embodiments, $R^1$ and $R^2$ may independently be a substituted or unsubstituted amine group represented by $NR^bR^c$.

In some example embodiments, $R^1$ and $R^2$ may independently be represented by one of Chemical Formulae A-1 to A-7.

In some example embodiments, $R^1$ and $R^2$ may be the same.

In some example embodiments, $R^1$ and $R^2$ may be different.

In some example embodiments, $L^1$ may be a fused ring of a substituted or unsubstituted C6 to C20 arylene group and a substituted or unsubstituted divalent C3 to C20 heterocyclic group and $R^1$ may be a substituted or unsubstituted amine group represented by $NR^bR^c$. The compound having such a structure may be represented by Chemical Formula 1A.

[Chemical Formula 1A]

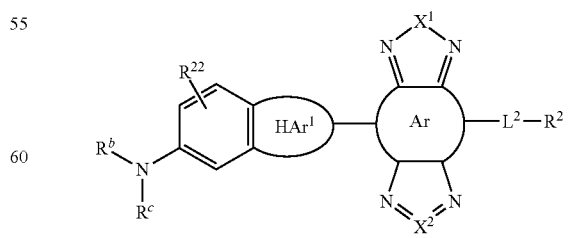

In Chemical Formula 1A, $X^1$, $X^2$, Ar, $L^2$, $R^2$, $R^b$, and $R^c$ are the same as described above, such that $X^1$ and $X^2$ are independently O, S, Se, Te, SO, $SO_2$, or $NR^a$, Ar is a substituted or unsubstituted C6 to C20 aromatic ring, $L^2$ is a single bond, a substituted or unsubstituted C6 to C20 arylene group, a substituted or unsubstituted divalent C3 to C20 heterocyclic group, a fused ring of a substituted or unsubstituted C6 to C20 arylene group and a substituted or unsubstituted divalent C3 to C20 heterocyclic group, or any combination thereof, $R^2$, $R^{22}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, and $R^b$ and $R^c$ are independently present or are linked with each other to form a ring, $HAr^1$ may be a heterocyclic group including a substituted or unsubstituted thiophenylene group, a substituted or unsubstituted furanylene group, a substituted or unsubstituted selenophenylene group, a substituted or unsubstituted tellurophenylene group, a substituted or unsubstituted pyrrolylene group, or any combination thereof, and $R^{22}$ may independently be hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof.

In some example embodiments, $L^1$ and $L^2$ may independently be a fused ring of a substituted or unsubstituted C6 to C20 arylene group and a substituted or unsubstituted divalent C3 to C20 heterocyclic group and $R^1$ and $R^2$ a may independently be a substituted or unsubstituted amine group represented by $NR^bR^c$. The compound having such a structure may be represented by Chemical Formula 1B.

[Chemical Formula 1B]

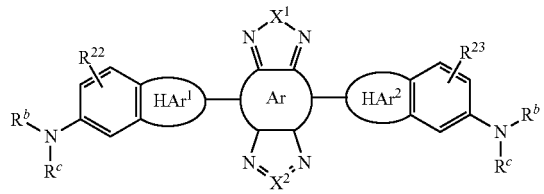

In Chemical Formula 1B, $X^1$, $X^2$, Ar, $R^b$, and $R^c$ are the same as described above, such that $X^1$ and $X^2$ are independently O, S, Se, Te, SO, $SO_2$, or $NR^a$, Ar is a substituted or unsubstituted C6 to C20 aromatic ring, $L^2$ is a single bond, a substituted or unsubstituted C6 to C20 arylene group, a substituted or unsubstituted divalent C3 to C20 heterocyclic group, a fused ring of a substituted or unsubstituted C6 to C20 arylene group and a substituted or unsubstituted divalent C3 to C20 heterocyclic group, or any combination thereof, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, $R^b$ and $R^c$ are independently present or are linked with each other to form a ring, each $R^b$ is the same or different, and each $R^c$ is the same or different, $HAr^1$ and $HAr^2$ may independently be a heterocyclic group including a substituted or unsubstituted thiophenylene group, a substituted or unsubstituted furanylene group, a substituted or unsubstituted selenophenylene group, a substituted or unsubstituted tellurophenylene group, a substituted or unsubstituted pyrrolylene group, or any combination thereof, and $R^{22}$, $R^{23}$, and $R^a$ may independently be hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof.

In some example embodiments, Ar may be benzene, $L^1$ and $L^2$ may independently be a fused ring of a substituted or unsubstituted C6 to C20 arylene group and a substituted or unsubstituted divalent C3 to C20 heterocyclic group, and $R^1$ and $R^2$ may independently be a substituted or unsubstituted amine group represented by $NR^bR^c$. The compound having such a structure may be represented by Chemical Formula 1C.

[Chemical Formula 1C]

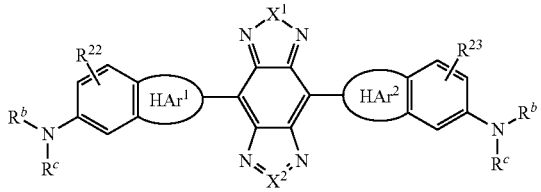

In Chemical Formula 1C, $X^1$, $X^2$, $HAr^1$, $HAr^2$, $R^{22}$, $R^{23}$, $R^b$, and $R^c$ are the same as described above, where $X^1$ and $X^2$ are independently O, S, Se, Te, SO, $SO_2$, or $NR^a$, $HAr^1$ and $HAr^2$ are independently a heterocyclic group including a substituted or unsubstituted thiophenylene group, a substituted or unsubstituted furanylene group, a substituted or unsubstituted selenophenylene group, a substituted or unsubstituted tellurophenylene group, a substituted or unsubstituted pyrrolylene group, or any combination thereof, $R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, each $R^b$ is the same or different, each $R^c$ is the same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, a halogen, or any combination thereof, and $R^b$ and $R^c$ are independently present or are linked with each other to form a ring.

The compound may be a light-absorbing material, for example a light-absorbing material absorbing light in a near infra-red wavelength region. In some example embodiments, a peak absorption wavelength of the compound may be for example greater than or equal to about 700 nm, greater than or equal to about 720 nm, greater than or equal to about 730 nm, greater than or equal to about 750 nm, greater than or equal to about 780 nm, greater than or equal to about 790 nm, greater than or equal to about 800 nm, greater than or equal to about 810 nm, greater than or equal to about 820 nm, greater than or equal to about 830 nm, greater than or equal to about 840 nm, greater than or equal to about 850 nm, greater than or equal to about 870 nm, greater than or equal to about 890 nm, greater than or equal to about 900 nm, or greater than or equal to about 910 nm. In some example embodiments, the peak absorption wavelength of the compound may belong to, in some example embodiments, about 700 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, about 830 nm to about 2000 nm, about 850 nm to about 1900 nm, about 870 nm to about 1800 nm, about 900 nm to about 1600 nm, or about 910 nm to about 1500 nm.

The compound may exhibit good charge transfer characteristics and accordingly has good photoelectric conversion characteristics for absorbing light and converting it into an electrical signal, so that it may be effectively used as a photoelectric conversion material of a photoelectric diode. A photoelectric device that includes the compound may have improved sensitivity in a low-illuminance environment and/or improved sensitivity to infrared/near infrared light. Accordingly, an organic sensor that includes such a photoelectric device may have improved sensitivity in a low-illuminance environment and/or improved sensitivity to infrared/near infrared light.

The compound may have good heat resistance and may prevent or reduce thermal decomposition during deposition, and thus may be repeatedly deposited. The compound may be thermally or vacuum deposited and may be deposited, in some example embodiments, by sublimation. In some example embodiments, deposition by sublimation may be confirmed by thermogravimetric analysis (TGA), and at a thermogravimetric analysis at a pressure of less than or equal to about 10 Pa, a temperature at which a 10% weight loss relative to an initial weight may be less than or equal to about 450° C. and a temperature at which a 50% weight loss relative to an initial weight may be less than or equal to about 500° C. In some example embodiments, at a thermogravimetric analysis of the compound at a pressure of less than or equal to about 10 Pa, for example temperature at which a 10% weight loss relative to an initial weight may be about 230° C. to about 450° C. and a temperature at which a 50% weight loss relative to an initial weight may be about 300° C. to about 500° C.

The compound may be manufactured in a form of a film.

The film may be applied to various fields requiring light absorption characteristics in a near infra-red wavelength region, for example a near infra-red absorption/cut film.

Since the compound has both light absorption characteristics and photoelectric characteristics in a near infra-red wavelength region, it may be effectively used as a photoelectric conversion material.

FIG. 1 is a cross-sectional view of a photoelectric diode according to some example embodiments.

Referring to FIG. 1, a photoelectric diode 100 according to some example embodiments includes a first electrode 10 and a second electrode 20 facing each other and an organic layer 30 disposed between the first electrode 10 and the second electrode 20.

A substrate (not shown) may be disposed at the side of the first electrode 10 or the second electrode 20. The substrate may be for example made of an inorganic material such as glass; an organic material such as polycarbonate, polymethylmethacrylate, polyethyleneterephthalate, polyethylenenaphthalate, polyamide, polyethersulfone, or any combination thereof, or a silicon wafer. The substrate may be omitted.

One of the first electrode 10 and the second electrode 20 is an anode and the other is a cathode. In some example embodiments, the first electrode 10 is a cathode and the second electrode 20 is an anode.

At least one of the first electrode 10 and the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AlTO), and fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). In some example embodiments, the first electrode 10 and the second electrode 20 may be all light-transmitting electrodes. In some example embodiments, the second electrode 20 may be a light receiving electrode disposed at a light receiving side.

The organic layer 30 may include an active layer.

The active layer is a layer including a p-type semiconductor and an n-type semiconductor to provide a pn junction, which is a layer producing excitons by receiving light from outside and then separating holes and electrons from the produced excitons.

The p-type semiconductor and the n-type semiconductor may be independently a light-absorbing material that absorbs light in at least one part of a wavelength region and the compound may be a p-type semiconductor or an n-type semiconductor. In some example embodiments, the compound may be used for a p-type semiconductor and fullerene or a fullerene derivative may be included as an n-type semiconductor but is not limited thereto.

The active layer may include an intrinsic layer in which an n-type semiconductor including the p-type semiconductor and a fullerene derivative are co-deposited. Herein, the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer may further include a p-type layer and/or an n-type layer in addition to the intrinsic layer. The p-type layer may include the p-type semiconductor and the n-type layer may include the n-type semiconductor. In some example embodiments, they may be included in various combinations of p-type layer/I layer, I layer/n-type layer, p-type layer/I layer/n-type layer, and the like.

The organic layer 30 effectively absorbs light in a wavelength spectrum ("wavelength region") of incident light (e.g., a near infra-red wavelength region) and may photoelectrically convert the absorbed wavelength spectrum of light into electric signals based on including the above-described compound. Restated, the organic layer 30 may be and/or include a film that includes the composition according to any of the example embodiments described herein, such that the organic layer 30 includes the compound according to any of the example embodiments as described herein. In some example embodiments, a peak absorption wavelength of the organic layer 30 may be greater than or equal to about 700 nm, greater than or equal to about 720 nm, greater than or equal to about 730 nm, greater than or equal to about 750 nm, greater than or equal to about 780 nm, greater than or equal to about 790 nm, greater than or equal to about 800 nm, greater than or equal to about 810 nm, greater than or equal to about 820 nm, greater than or equal to about 830 nm, greater than or equal to about 840 nm, greater than or equal to about 850 nm, greater than or equal to about 870 nm, greater than or equal to about 890 nm, greater than or equal to about 900 nm, or greater than or equal to about 910 nm. The peak absorption wavelength of the organic layer 30 may belong to a wavelength region of, for example about 700 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, about 830 nm to about 2000 nm, about 850 nm to about 1900 nm, about 870 nm to about 1800 nm, about 900 nm to about 1600 nm, or about 910 nm to about 1500 nm.

The organic layer 30 may further include a charge auxiliary layer (not shown) between the first electrode 10 and the active layer and/or the second electrode 20 and the active layer. The charge auxiliary layer may make holes and electrons separated in the active layer 30 be transported easily to improve efficiency.

The charge auxiliary layer may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layer may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The charge auxiliary layer may include for example the compound.

The photoelectric diode 100 may further include an anti-reflection layer (not shown) on one surface of the first electrode 10 or the second electrode 20. The anti-reflection layer is disposed at a light incidence side and lowers reflectance of light of incident light and thereby light absorbance is further improved. In some example embodiments, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5 and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or any combination thereof; a metal sulfide such as zinc sulfide; or an organic material such as an amine derivative, but is not limited thereto.

In the photoelectric diode 100, when light enters from the first electrode 10 or the second electrode 20 and the organic layer 30 absorbs light in a predetermined wavelength region, excitons may be produced thereinside. The excitons are separated into holes and electrons in the organic layer 30, and the separated holes are transported to an anode that is one of the first electrode 10 and the second electrode 20 and the separated electrons are transported to the cathode that is the other of the first electrode 10 and the second electrode 20 so as to flow a current.

The photoelectric diode 100 may be applied to a solar cell, an image sensor, a photodetector, and a photosensor, but is not limited thereto.

The photoelectric diode may be for example applied to an organic sensor. The organic sensor may be an organic CMOS sensor, for example an organic CMOS infrared light sensor or an organic CMOS image sensor.

Figure 2:
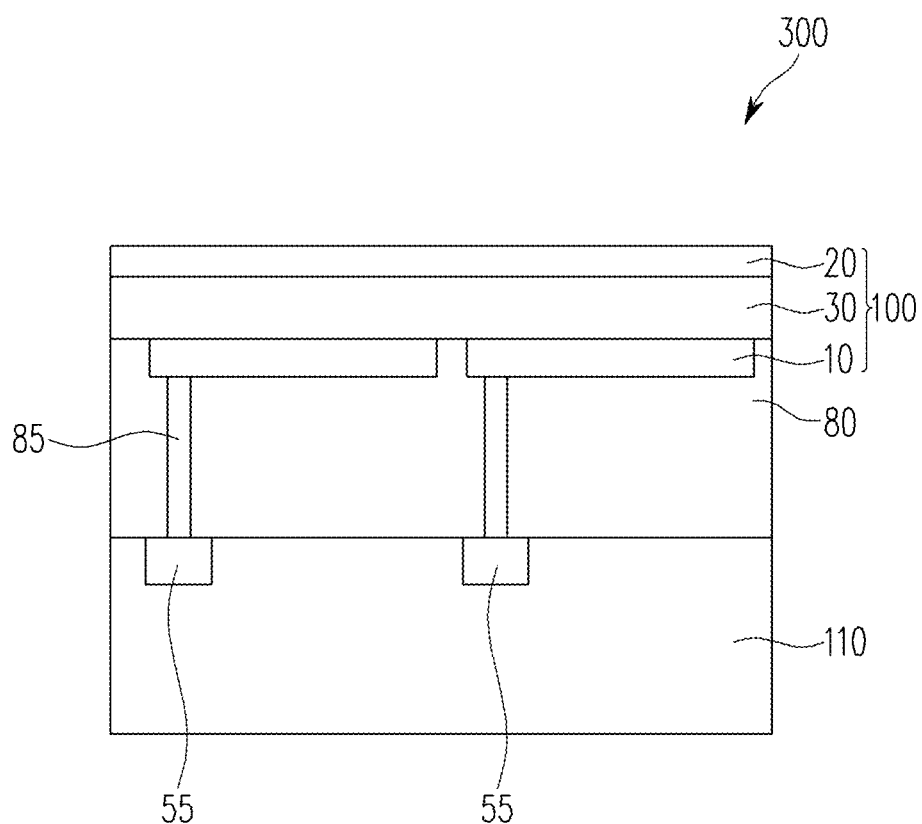
FIG. 2 is a cross-sectional view showing an example of an organic sensor according to some example embodiments.

FIG. 2 is a cross-sectional view showing an example of an organic sensor according to some example embodiments.

The organic sensor 300 according to some example embodiments includes a semiconductor substrate 110, an insulation layer 80, and a photoelectric diode 100.

The semiconductor substrate 110 may be a silicon substrate and is integrated with a transmission transistor (not shown) and a charge storage 55. The charge storage 55 may be integrated in each pixel. The charge storage 55 is electrically connected to the photoelectric diode 100 that will be described later and information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, in some example embodiments, aluminum (Al), copper (Cu), silver (Ag), and alloys thereof, but are not limited thereto. Further, it is not limited to the structure, and the metal wire and pad may be disposed under the semiconductor substrate 110.

The insulation layer 80 is formed on the metal line and pad. The insulation layer 80 may be made of an inorganic insulating material such as a silicon oxide and/or a silicon nitride, or a low dielectric constant (low K) material such as SiC, SiCOH, SiCO, and SiOF. The insulation layer 60 has a trench 85 exposing the charge storage 55. The trench 85 may be filled with fillers.

The photoelectric diode 100 is formed on the insulation layer 80. As described above, the photoelectric diode 100 includes a first electrode 10, an organic layer 30, and a second electrode 20. Even though a structure in which the first electrode 10, the organic layer 30 and the second electrode 20 are sequentially stacked is shown as an example in the drawing, the present disclosure is not limited to this structure, and the second electrode 20, the organic layer 30, and the electrodes 10 may be arranged in this order.

The first electrode 10 and the second electrode 20 may both be transparent electrodes, and the organic layer 30 is the same as described above. The organic layer 30 may selectively absorb light in a near infra-red wavelength region. Incident light from the side of the second electrode 20 may be photoelectrically converted by mainly absorbing light in a near infra-red wavelength region in the organic layer 30.

Focusing lens (not shown) may be further formed on the photoelectric diode 100. The focusing lens may control a direction of incident light and gather the light in one region. The focusing lens may have a shape of, in some example embodiments, a cylinder or a hemisphere, but is not limited thereto.

The organic sensor according to some example embodiments may be an organic infrared light sensor, for example an iris sensor or a depth sensor.

The iris sensor identifies a person by using unique iris characteristics of every person and specifically, taking an image of an eye of a user within an appropriate distance, processing the image, and comparing it with his/her stored image.

The depth sensor identifies a shape and a location of an object from its three-dimensional information by taking an image of the object within an appropriate distance with a user and processing the image. This depth sensor may be for example used as a face recognition sensor.

Figure 3:
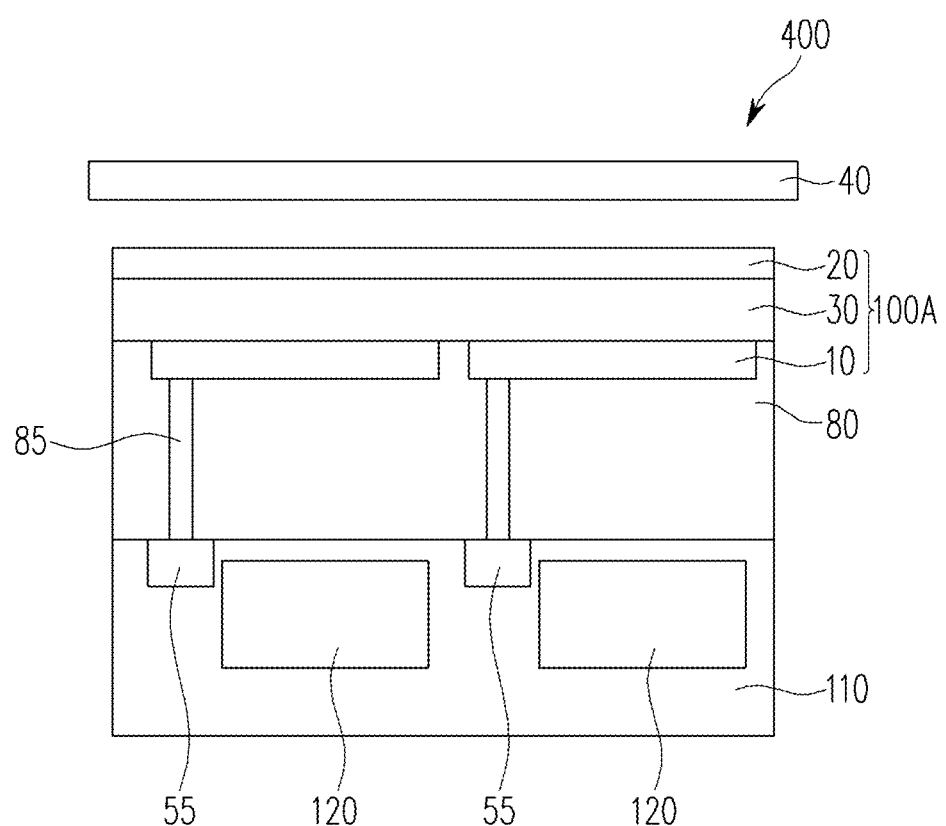
FIG. 3 is a cross-sectional view showing an example of an organic sensor according to some example embodiments.

FIG. 3 is a cross-sectional view showing an example of an organic sensor according to some example embodiments.

The organic sensor according to some example embodiments may include a plurality of sensors having different functions. In some example embodiments, at least one of the plurality of sensors having different functions may be a biometric sensor, and the biometric sensor may be for example an iris sensor, a depth sensor, a fingerprint sensor, a blood vessel distribution sensor, and the like, but is not limited thereto. In some example embodiments, one of the plurality of sensors having different functions may be an iris sensor and the other may be a depth sensor.

In some example embodiments, a plurality of sensors may include, for example a first infrared light sensor configured to sense light in an infrared region having a first wavelength ($\lambda_1$) in a near infra-red wavelength region and a second infrared light sensor configured to sense light in an infrared region having a second wavelength ($\lambda_2$) in a near infra-red wavelength region.

The first wavelength ($\lambda_1$) and the second wavelength ($\lambda_2$) may be for example different in a wavelength region of about 750 nm to about 3000 nm, and for example a difference between the first wavelength ($\lambda_1$) and the second wavelength ($\lambda_2$) may be greater than or equal to about 30 nm, greater than or equal to about 50 nm, greater than or equal to about 70 nm, greater than or equal to about 80 nm, or greater than or equal to about 90 nm.

In some example embodiments, one of the first wavelength ($\lambda_1$) and the second wavelength ($\lambda_2$) may belong to a wavelength region of about 780 nm to about 900 nm and the other of the first wavelength ($\lambda_1$) and the second wavelength ($\lambda_2$) may belong to a wavelength region of about 830 nm to about 1000 nm.

In some example embodiments, one of the first wavelength ($\lambda_1$) and the second wavelength ($\lambda_2$) may belong to a wavelength region of about 780 nm to about 840 nm and the other of the first wavelength ($\lambda_1$) and the second wavelength ($\lambda_2$) may belong to a wavelength region of about 910 nm to about 970 nm.

In some example embodiments, one of the first wavelength ($\lambda_1$) and the second wavelength ($\lambda_2$) may belong to a wavelength region of about 800 nm to about 830 nm and the other of the first wavelength ($\lambda_1$) and the second wavelength ($\lambda_2$) may belong to a wavelength region of about 930 nm to about 950 nm.

In some example embodiments, one of the first wavelength ($\lambda_1$) and the second wavelength ($\lambda_2$) may belong to a wavelength region of about 805 nm to about 815 nm and the other of the first wavelength ($\lambda_1$) and the second wavelength ($\lambda_2$) may belong to a wavelength region of about 935 nm to about 945 nm.

In some example embodiments, one of the first wavelength ($\lambda_1$) and the second wavelength ($\lambda_2$) may about 810 nm and the other of the first wavelength ($\lambda_1$) and the second wavelength ($\lambda_2$) may be about 940 nm.

The organic sensor 400 according to some example embodiments includes a dual bandpass filter 40, a first infrared light sensor 100A, an insulation layer 80, and a semiconductor substrate 110 integrated with a second infrared light sensor 120. The first infrared light sensor 100A and the second infrared light sensor 120 may be stacked.

The dual bandpass filter 40 may be disposed on a front side of the organic sensor 400 and may selectively transmit infrared light including the first wavelength ($\lambda_1$) and infrared light including the second wavelength ($\lambda_2$) and may block and/or absorb other light. Herein, other light may include light in an ultraviolet (UV) and visible region.

The first infrared light sensor 100A may be the photoelectric diode 100 according to some example embodiments and details thereof are omitted.

The second infrared light sensor 120 may be integrated in the semiconductor substrate 110 and may be a photo-sensing device. The semiconductor substrate 110 may be for example a silicon substrate and may be integrated with the second infrared light sensor 120, the charge storage 55, and a transmission transistor (not shown).

The second infrared light sensor 120 may be a photodiode and may sense entered light, and sensed information is transferred by the transmission transistor. Herein, the light entered into the second infrared light sensor 120 is light that passes the dual bandpass filter 40 and the first infrared light sensor 100A and may be infrared light in a predetermined region including the second wavelength ($\lambda_2$). All infrared light in a predetermined region including the first wavelength ($\lambda_1$) may be absorbed by the organic layer 30 and may not reach the second infrared light sensor 120. In this case, a separate filter for wavelength selectivity with respect to the light entered into the second infrared light sensor 120 is not separately needed. However, for the time when all infrared light in a predetermined region including the first wavelength ($\lambda_1$) is not absorbed by organic layer 30, a filter between the first infrared light sensor 100A and the second infrared light sensor 120 may be further disposed.

The organic sensor according to some example embodiments may include two infrared light sensors respectively performing separately functions and thus may work as a combination sensor. In addition, two sensors performing separately functions are stacked in each pixel, and thus the number of pixel performing functioning of each sensor is twice increased while maintaining a size and resultantly, sensitivity may be much improved.

Figure 4:
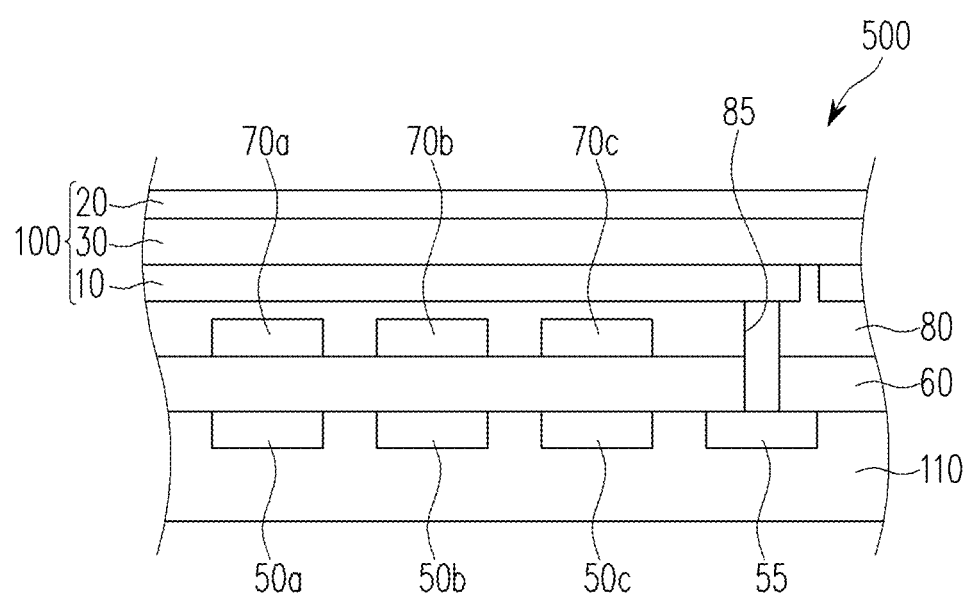
FIG. 4 is a cross-sectional view showing an example of an organic sensor according to some example embodiments.
Figure 5:
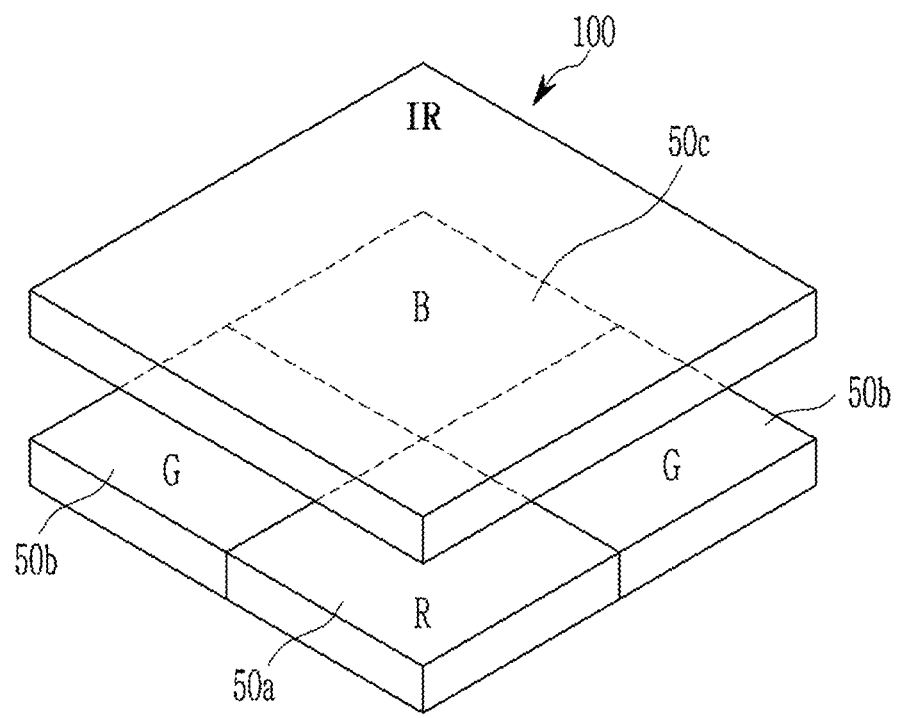
FIG. 5 is a perspective view of the organic sensor of FIG. 4 according to some example embodiments.

FIG. 4 is a cross-sectional view showing an example of an organic sensor according to some example embodiments. FIG. 5 is a perspective view of the organic sensor of FIG. 4 according to some example embodiments.

An organic sensor according to some example embodiments may be an organic CMOS image sensor.

Referring to FIG. 4, an organic sensor 500 according to some example embodiments includes a semiconductor substrate 110 integrated with photo-sensing devices 50a, 50b, and 50c, a transmission transistor (not shown), and a charge storage 55, a lower insulation layer 60, color filters 70a, 70b, and 70c, an upper insulation layer 80, and a photoelectric diode 100.

The semiconductor substrate 110 may be integrated with photo-sensing devices 50a, 50b, and 50c, a transmission transistor (not shown), and a charge storage 55. The photo-sensing devices 50a, 50b, and 50c may be photodiodes.

The photo-sensing devices 50a, 50b, and 50c, the transmission transistor, and/or the charge storage 55 may be integrated in each pixel. In some example embodiments, the photo-sensing device 50a may be included in a red pixel, the photo-sensing device 50b may be included in a green pixel, and the photo-sensing device 50c may be included in a blue pixel.

The photo-sensing devices 50a, 50b, and 50c sense light, the information sensed by the photo-sensing devices may be transferred by the transmission transistor, the charge storage 55 is electrically connected to the photoelectric diode 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, in some example embodiments, aluminum (Al), copper (Cu), silver (Ag), and alloys thereof, but are not limited thereto. Further, it is not limited to the structure, and the metal wire and pad may be disposed under the photo-sensing devices 50a and 50b.

The lower insulation layer 60 is formed on the metal wire and the pad.

Color filters 70a, 70b, and 70c are formed on the lower insulation layer 60. The color filters 70a, 70b, and 70c includes a red filter 70a formed in a red pixel, a green filter 70b formed in a green pixel, and a blue filter 70c formed in a blue pixel. Each color filter 70a, 70b, 70c may be configured to selectively transmit a particular wavelength spectrum of incident light to a particular corresponding photo-sensing device 50a, 50b, 50c, the particular wavelength spectrum of incident light including at least the particular wavelength spectrum of incident light that the corresponding photo-sensing device 50a, 50b, 50c is configured to absorb (i.e., detect), such that the corresponding photo-sensing device 50a, 50b, 50c is configured to absorb the particular wavelength spectrum of incident light.

The upper insulation layer 80 is formed on the color filters 70a, 70b, and 70c. The upper insulation layer 80 eliminates steps caused by the color filters 70a, 70b, and 70c and planarizes the surface.

The photoelectric diode 100 is formed on the upper insulation layer 80. As described above, the photoelectric diode 100 includes a first electrode 10, an organic layer 30, and a second electrode 20. Even though a structure in which the first electrode 10, the organic layer 30 and the second electrode 20 are sequentially stacked is shown as an example in the drawing, the present disclosure is not limited to this structure, and the second electrode 20, the organic layer 30, and the electrodes 10 may be arranged in this order.

The first electrode 10 and the second electrode 20 may both be transparent electrodes, and the organic layer 30 is the same as described above. The organic layer 30 may selectively absorb light in a near infra-red wavelength region.

Incident light from the side of the second electrode 20 may be photoelectrically converted by mainly absorbing light in a near infra-red wavelength region in the organic layer 30. Light in the remaining wavelength region may pass through the first electrode 10 and the color filters 70a, 70b, and 70c, the light in a red wavelength region passing through the color filter 70a may be sensed by the photo-sensing device 50a, the light in a green wavelength region passing through the color filter 70b may be sensed by the photo-sensing device 50b, and the light in a blue wavelength region passing through the color filter 70c may be sensed by the photo-sensing device 50c.

The organic sensor may be applied to various electronic devices, for example and the electronic devices may include for example a camera, a camcorder, a mobile phone internally having them, a display device, a security device, or a medical device, but are not limited thereto.

Figure 6:
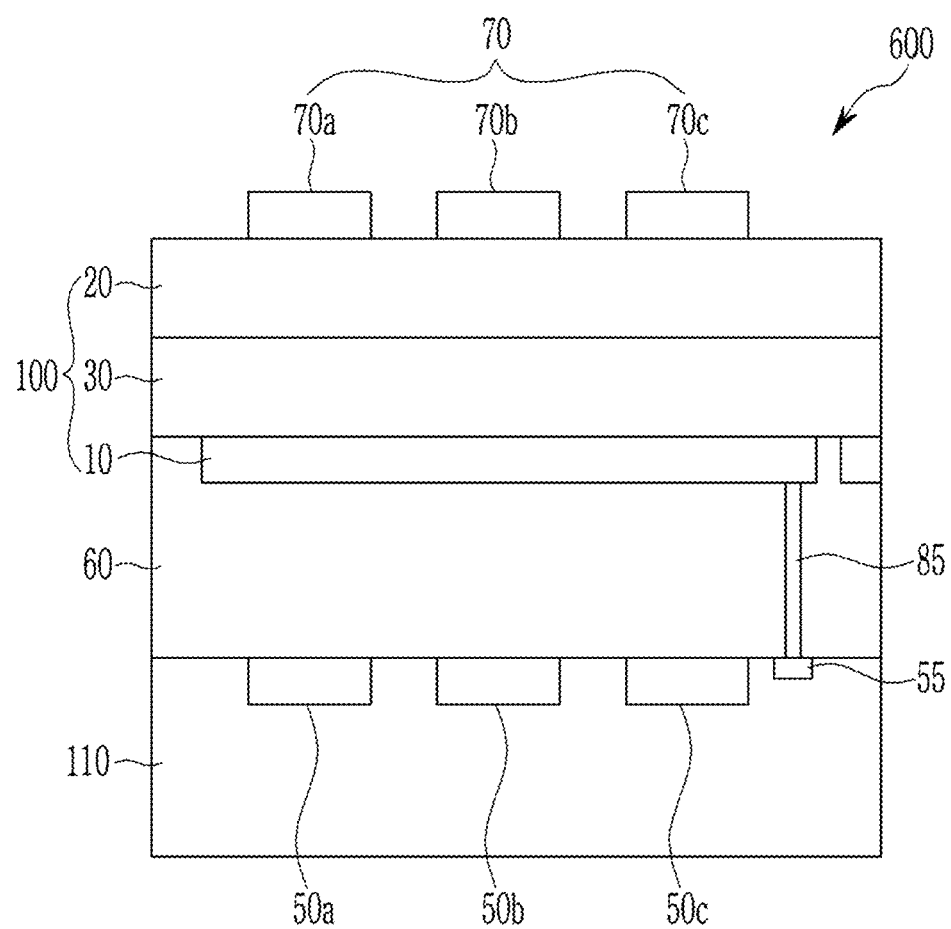
FIG. 6 is a schematic cross-sectional view of an organic sensor according to some example embodiments.

FIG. 6 is a schematic cross-sectional view of an organic sensor according to some example embodiments.

Referring to FIG. 6, an organic sensor 600 according to some example embodiments includes a semiconductor substrate 110 integrated with photo-sensing devices 50a, 50b, and 50c, a transmission transistor (not shown) and a charge storage 55, a lower insulation layer 60, a color filter layer 70 including color filters 70a, 70b, and 70c, and a photoelectric device 100. As shown in FIG. 6, the photoelectric device 100 may be between the semiconductor substrate 110 and the color filter layer 70, such that the color filter layer 70 is distal from the photo-sensing devices 50a, 50b, and 50c in relation to the photoelectric device 100. Other structures are the same as the organic sensor of FIG. 4. In some example embodiments, the color filter layer 70 may include color filters configured to filter a mixture of wavelength spectra of light (e.g., mixed colors). For example, in FIG. 6, color filter 70a may be configured to filter magenta light, color filter 70b may be configured to filter cyan light, and color filter 70b may be configured to filter yellow light, while photo-sensing device 50a may be configured to detect ("sense") blue light and photo-sensing device 50b may be configured to detect red light.

Figure 7:
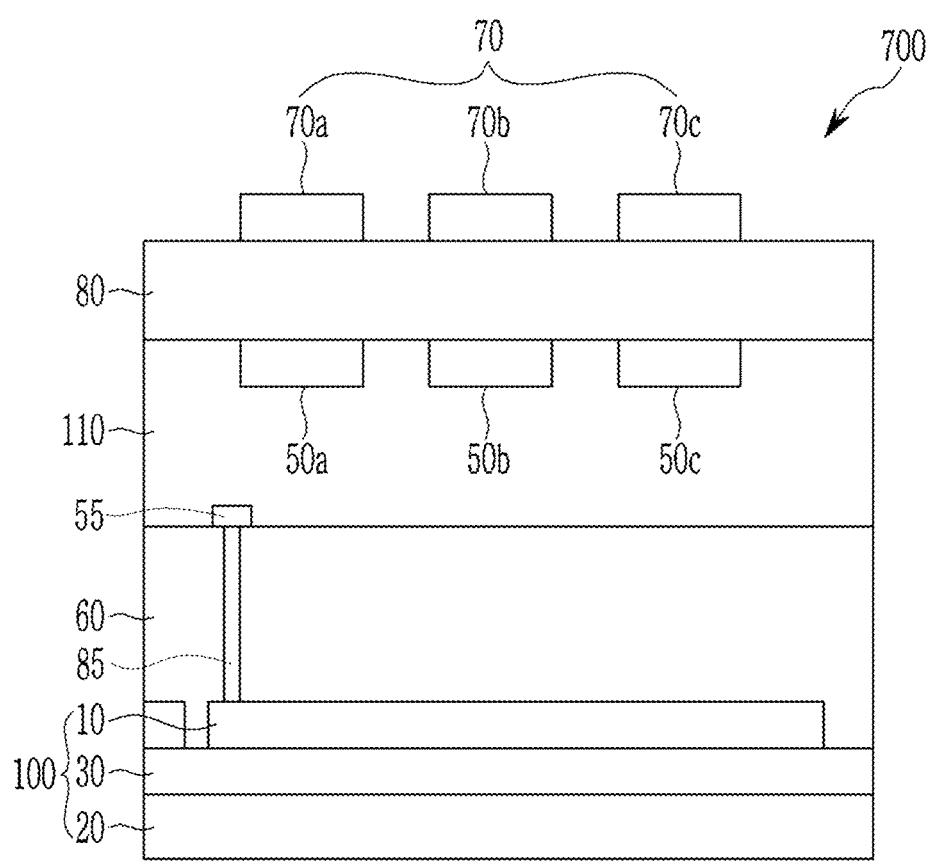
FIG. 7 is a schematic cross-sectional view of an organic sensor according to some example embodiments.

FIG. 7 is a schematic cross-sectional view of an organic sensor according to some example embodiments.

Referring to FIG. 7, an organic image sensor 700 according to some example embodiments includes a semiconductor substrate 110 integrated with photo-sensing devices 50a, 50b, and 50c, a transmission transistor (not shown) and a charge storage 55, a lower insulation layer 60, a color filter layer 70, and an upper insulation layer 80 on the semiconductor substrate 110, and a photoelectric device 100 under the semiconductor substrate 110. As shown in FIG. 7, the photoelectric device 100 may be on (e.g., above or beneath) the semiconductor substrate 110, such that the color filter layer 70 is distal from the photoelectric device 100 in relation to the photo-sensing devices 50a, 50b, and 50c. Other structures are the same as the organic sensor of FIG. 4.

Figure 8:
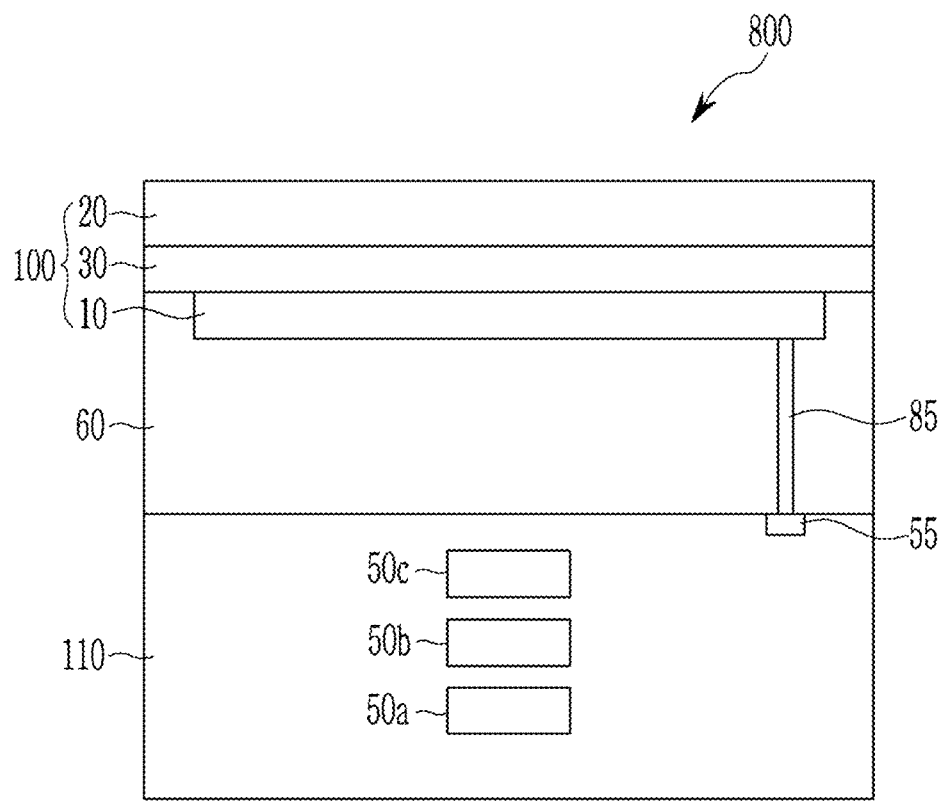
FIG. 8 is a cross-sectional view showing an organic sensor according to some example embodiments.

FIG. 8 is a cross-sectional view showing an organic sensor according to some example embodiments.

An organic sensor 800 according to some example embodiments includes a semiconductor substrate 110 integrated with photo-sensing devices 50a, 50b, and 50c, a transmission transistor (not shown), and a charge storage 55, an insulation layer 60 having a trench 85, and a photoelectric device 100.

In the organic sensor 800 according to some example embodiments, the photo-sensing devices 50a, 50b, and 50c are stacked in a vertical direction and the color filter layer 70 is omitted. The photo-sensing devices 50a, 50b, and 50c are electrically connected to charge storage (not shown) and may be transferred by the transmission transistor. The photosensing devices 50*a*, 50*b*, and 50*c* may selectively absorb light in each wavelength spectrum of light depending on a stack depth. Other structures are the same as the organic sensor of FIG. 4.

Figure 9:
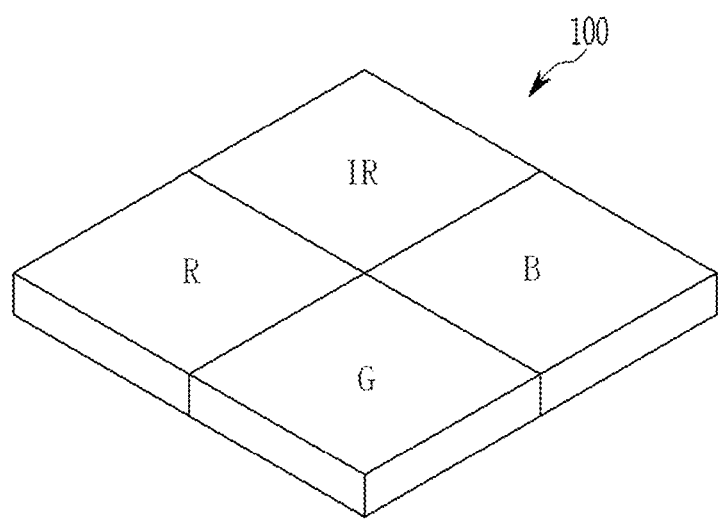
FIG. 9 is a perspective view of an organic sensor according to some example embodiments.
Figure 10:
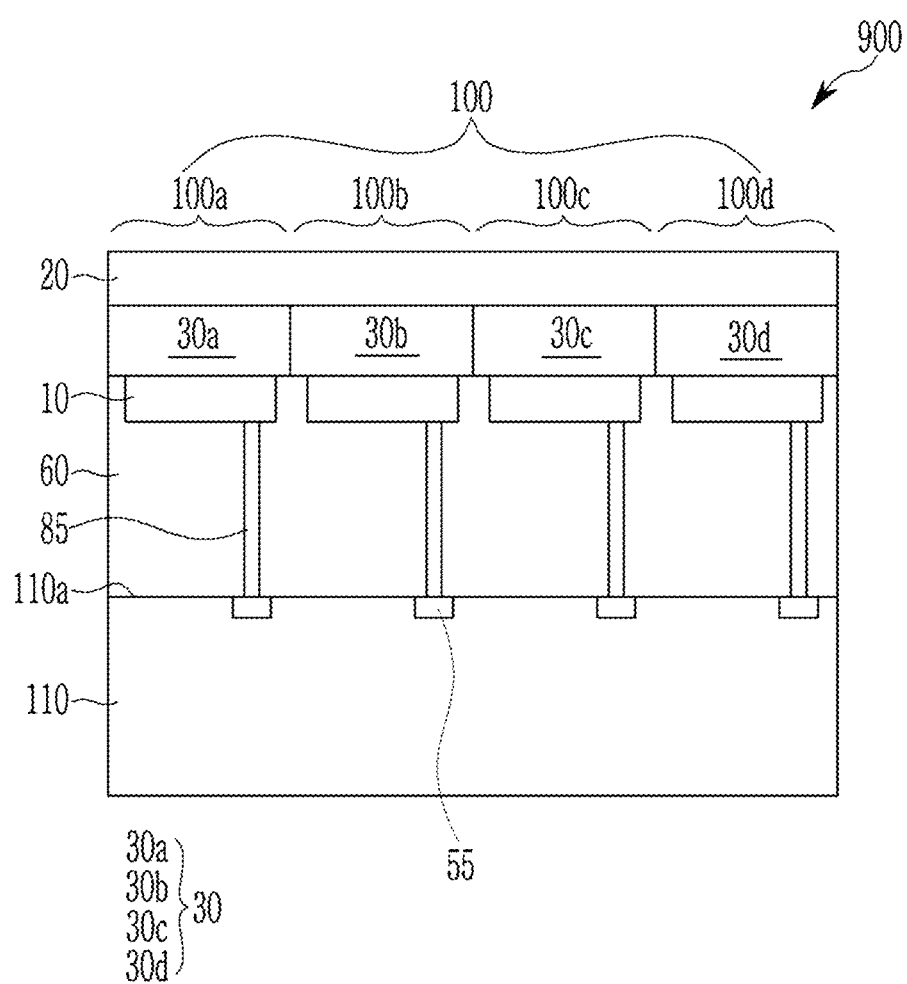
FIG. 10 is a schematic cross-sectional view showing the organic sensor of FIG. 9 according to some example embodiments.

FIG. 9 is a perspective view of an organic sensor according to some example embodiments. FIG. 10 is a schematic cross-sectional view showing the organic sensor of FIG. 9, according to some example embodiments.

As shown with reference to FIG. 10, an organic sensor 900 may include a photoelectric device 100 that includes a plurality of photoelectric devices 100*a*, 100*b*, 100*c*, and 100*d* on a semiconductor substrate 110, where the plurality of photoelectric devices 100*a*, 100*b*, 100*c*, and 100*d* are configured to absorb and convert different ones of blue light, green light, red light, or infrared light (i.e., different wavelength spectra of incident light) into electric signals, respectively.

Referring to FIG. 10, an organic CMOS image sensor 800 according to some example embodiments includes a semiconductor substrate 110 integrated with charge storages 55, transmission transistors (not shown), an insulation layer 60, and photoelectric devices 100*a*-100*d*.

As shown with reference to FIGS. 9-10, an organic sensor 900 may include a photoelectric device 100 that itself includes a plurality of photoelectric devices 100*a*-100*d* on a semiconductor substrate 110, where the plurality of photoelectric devices 100*a*-100*d* are configured to absorb and convert different ones of blue light, green light, red light, or infrared light (i.e., different wavelength spectra of incident light) into electric signals, respectively. As shown in FIG. 10, the separate photoelectric devices 100*a*-100*d* may be horizontally arranged on the semiconductor substrate 110 such that the photoelectric devices 100*a*-100*d* are partially or entirely overlapped with each other in a direction that extends in parallel with a top surface 110*a* of the semiconductor substrate 110. As shown, each separate photoelectric device 100*a* to 100*d* is connected to a separate charge storage 55 that is integrated into the semiconductor substrate 110 via a separate trench 85.

Each photoelectric device 100*a* to 100*d* may be any one of the photoelectric devices described herein. In some example embodiments, separate photoelectric devices 100*a* to 100*d* may include different portions of a common, continuous layer that extends continuously between two or more of the photoelectric devices 100*a* to 100*d*. In some example embodiments, the photoelectric devices 100*a* to 100*d* may share a common opposed electrode 20. In another example, two or more of the photoelectric devices 100*a* to 100*d* may have different photoelectric conversion layers 30*a*, 30*b*, 30*c*, and 30*d* that are configured to absorb different wavelength spectra of incident light. Other structures are the same as the organic sensor of FIG. 4.

Figure 11:
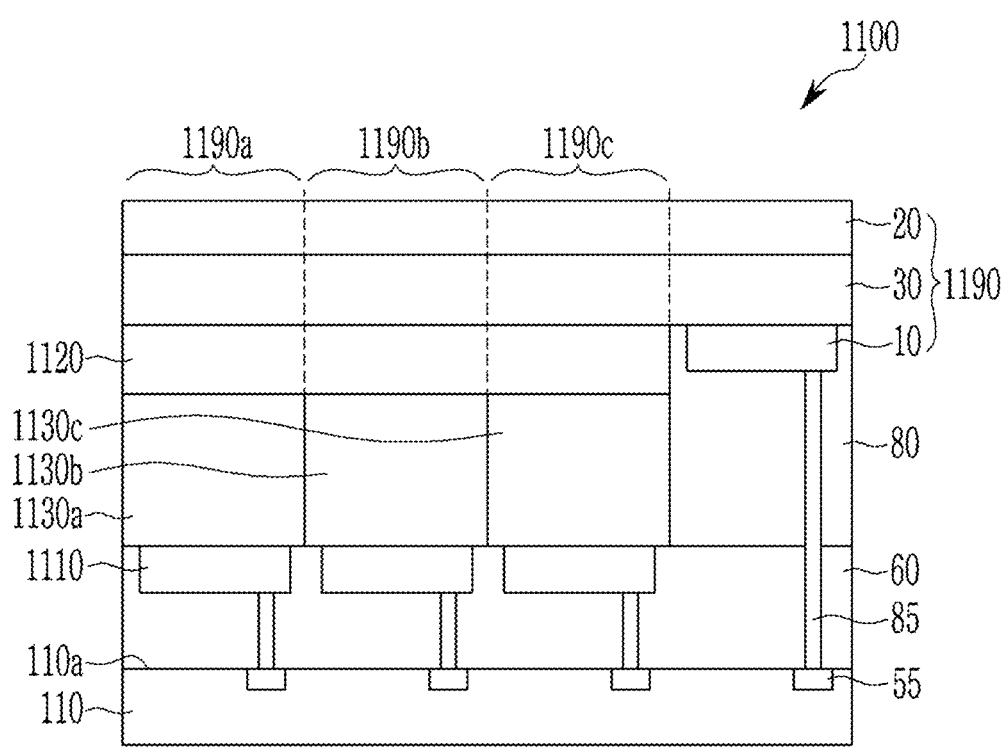
FIG. 11 is a schematic cross-sectional view of an organic sensor according to some example embodiments.

FIG. 11 is a schematic cross-sectional view of an organic sensor according to some example embodiments.

Referring to FIG. 11, an organic CMOS image sensor 1100 includes a semiconductor substrate 110 integrated with charge storages, transmission transistors (not shown), an intermediate insulation layer 60, a first photoelectric device 1190, a second photoelectric device 1190*a*, a third photoelectric device 1190*b*, and a fourth photoelectric device 1190*c*. The first photoelectric device 1190, which may be an infrared/near infrared photoelectric device and thus may be configured to absorb infrared and/or near infrared light, is formed on an entire surface of the second to fourth photoelectric devices 1190*a* to 1190*c*. The second to fourth photoelectric devices 1190*a*, 1190*b*, and 1190*c* may be configured to absorb and convert different ones of blue light, green light, and red light (i.e., different wavelength spectra of incident light), respectively. For example, as shown, the second to fourth photoelectric devices 1190*a*, 1190*b*, and 1190*c* may share a continuous opposed electrode 1120 and may include separate, respective pixel electrodes 1110 and may further each include separate, respective photoelectric conversion layers 1130*a*, 1130*b*, and 1130*c* that may be configured to absorb and convert separate, respective wavelength spectra of light (e.g., red light, green light, and blue light, respectively). Other structures are the same as the image sensor of FIG. 4.

Referring to FIG. 11, the first photoelectric device 1190 may be stacked on the second to fourth photoelectric device 1190*a* to 1190*c* so as to at least partially overlap in a direction extending perpendicular to the top surface 110*a* of the semiconductor substrate 110, and wherein the second to fourth photoelectric devices 1190*a* to 1190*c* overlap in a direction extending parallel to the top surface 110*a* of the semiconductor substrate 110. It will be understood that, in some example embodiments, the second to fourth photoelectric devices 1190*a* to 1190*c* include multiple, horizontally-arranged photoelectric devices configured to absorb different wavelengths spectra of light while the first photoelectric device 1190 is limited to a single photoelectric device that is configured to absorb a single wavelength spectrum of light. In some example embodiments, including the example embodiments shown in FIG. 11, an entirety of the first photoelectric device 1190 overlaps a limited portion of the second to fourth photoelectric devices 1190*a* to 1190*c* in the direction extending perpendicular to the top surface 110*a* and a remainder portion of the first photoelectric device 1190 that is exposed by the second to fourth photoelectric devices 1190*a* to 1190*c* is covered by insulation layer 80. However, it will be understood that in some example embodiments an entirety of the first photoelectric device 1190 overlaps a limited portion of the second to fourth photoelectric devices 1190*a* to 1190*c* in the direction extending perpendicular to the top surface 110*a*.

Figure 12:
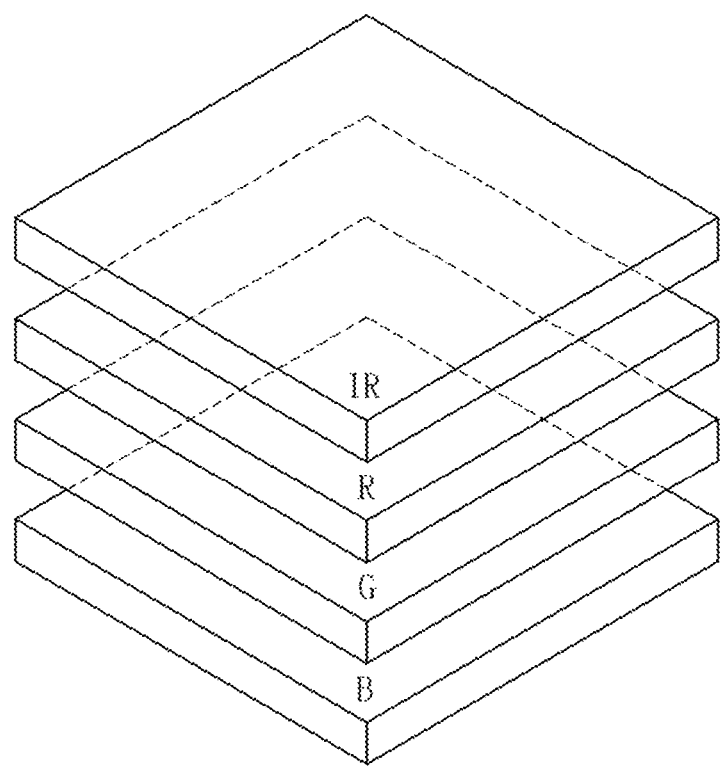
FIG. 12 is a perspective view of an organic sensor according to some example embodiments.
Figure 13:
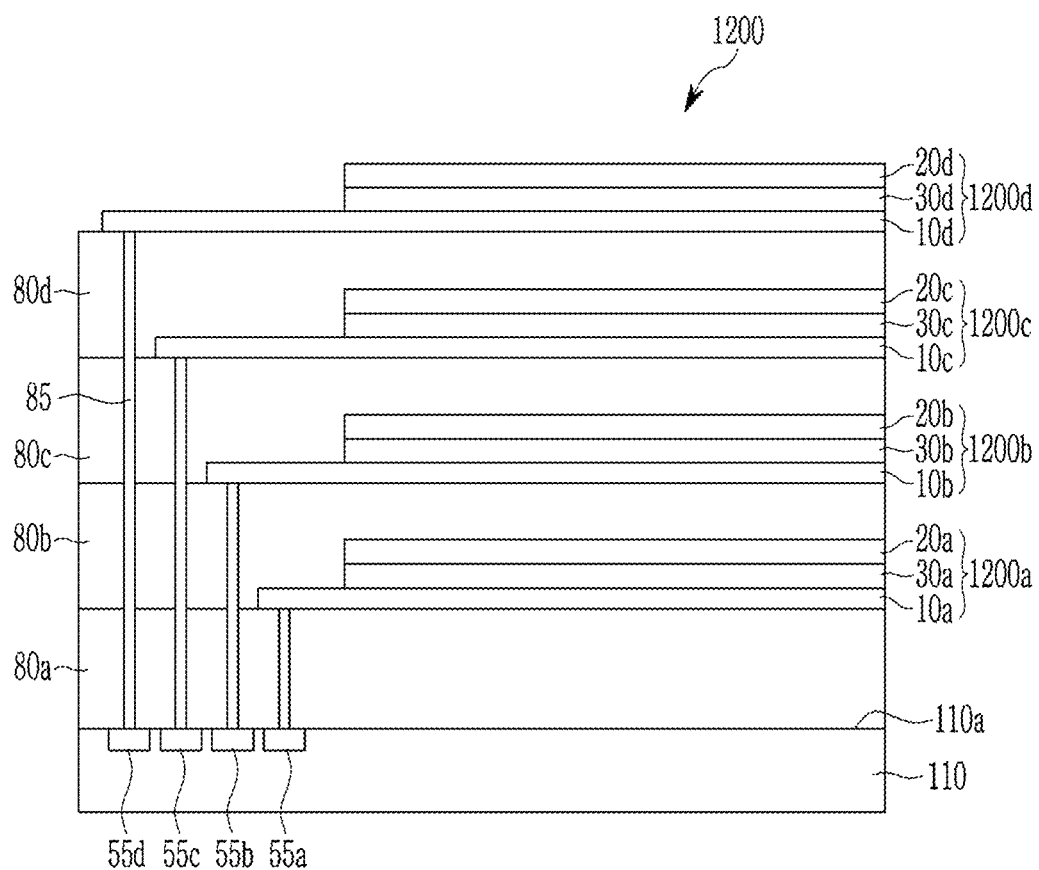
FIG. 13 is a schematic cross-sectional view showing the organic sensor of FIG. 12 according to some example embodiments.

FIG. 12 is a perspective view of an organic sensor according to some example embodiments, and FIG. 13 is a schematic cross-sectional view showing the organic sensor of FIG. 12 according to some example embodiments.

The organic sensor 1200 according to some example embodiments includes an infrared/near infrared photoelectric device configured to selectively absorb light in an infrared/near infrared wavelength spectrum of light, a red photoelectric device configured to selectively absorb and convert (into electric signals) light in a red wavelength spectrum of incident light, a green photoelectric device configured to selectively absorb and convert (into electric signals) light in a green wavelength spectrum of incident light, a blue photoelectric device configured to selectively absorb and convert (into electric signals) light in a blue wavelength spectrum of incident light, and they are stacked.

The organic sensor 1200 according to some example embodiments includes a semiconductor substrate 110, a lower insulation layer 80*a*, an intermediate insulation layer 80*b*, another intermediate insulation layer 80*c*, an upper insulation layer 80*d*, a first photoelectric device 1200*a*, a second photoelectric device 1200*b*, a third photoelectric device 1200*c*, and a fourth photoelectric device 1200*d*. As shown, the first to fourth photoelectric devices 1200*a* to 1200*d* are stacked vertically on the semiconductor substrate 110, such that the first to fourth photoelectric devices 1200*a* to 1200*d* overlap each other in a direction extending parallel to a top surface 110*a* of the semiconductor substrate 110.

The semiconductor substrate 110 may be a silicon substrate, and is integrated with the transmission transistor (not shown) and the charge storages 55a, 55b, 55c, and 55d.

The first photoelectric device 1200a is formed on the lower insulation layer 80a. The first photoelectric device 1200a includes a first electrode 10a and a second electrode 20a facing each other and a photoelectric conversion layer 30a between the first electrode 10a and the second electrode 20a. The first electrode 10a, the second electrode 20a, and the photoelectric conversion layer 30a are the same as described above and the photoelectric conversion layer 30a may selectively absorb and convert (into electric signals) light in one of infrared, red, blue, and green wavelength spectra of incident light. For example, the first photoelectric device 1200a may be a blue photoelectric device. In the drawing, the first electrode 10a, the photoelectric conversion layer 30a, and the second electrode 20a are sequentially stacked, but this disclosure is not limited thereto, and for example they may be stacked in an order of the second electrode 20a, the photoelectric conversion layer 30a, and the first electrode 10a.

An intermediate insulation layer 80b is formed on the first photoelectric device 1200a.

The second photoelectric device 1200b is formed on the intermediate insulation layer 80b. The second photoelectric device 1200b includes a first electrode 10b and a second electrode 20b facing each other and a light-absorption layer 30b (e.g., photoelectric conversion layer 30b) between the first electrode 10b and the second electrode 20b. The first electrode 10b, the second electrode 20b, and the photoelectric conversion layer 30b may be described above and the photoelectric conversion layer 30b may selectively absorb and convert (into electric signals) light in one of infrared, red, blue, and green wavelength spectra of incident light. For example, the second photoelectric device 1200b may be a green photoelectric device. In the drawing, the first electrode 10b, the photoelectric conversion layer 30b, and the second electrode 20b are sequentially stacked, but this disclosure is not limited thereto, and for example they may be stacked in an order of the second electrode 20b, the photoelectric conversion layer 30b, and the first electrode 10b.

Another intermediate insulation layer 80c is formed on the second photoelectric device 1200b.

The third photoelectric device 1200c is formed on the intermediate insulation layer 80c. The third photoelectric device 1200c includes a first electrode 10c and a second electrode 20c facing each other and a light-absorption layer 30c (e.g., photoelectric conversion layer 30c) between the first electrode 10c and the second electrode 20c. The first electrode 10c, the second electrode 20c, and the photoelectric conversion layer 30c may be described above and the photoelectric conversion layer 30c may selectively absorb and convert (into electric signals) light in one of infrared, red, blue, and green wavelength spectra of incident light. For example, the third photoelectric device 1200c may be a red photoelectric device. In the drawing, the first electrode 10c, the photoelectric conversion layer 30c, and the second electrode 20c are sequentially stacked, but this disclosure is not limited thereto, and for example they may be stacked in an order of the second electrode 20c, the photoelectric conversion layer 30c, and the first electrode 10c.

The upper insulation layer 80d is formed on the third photoelectric device 1200c.

The lower insulation layer 80a, the intermediate insulation layers 80b and 80c, and the upper insulation layer 80d have a plurality of through-holes exposing the charge storages 55a, 55b, 55c, and 55d.

The fourth photoelectric device 1200d is formed on the upper insulation layer 80d. The fourth photoelectric device 1200d includes a first electrode 10d and a second electrode 20d facing each other and a light-absorption layer 30d (e.g., photoelectric conversion layer 30d) between the first electrode 10d and the second electrode 20d. The first electrode 10d, the second electrode 20d, and the photoelectric conversion layer 30d may be described above and the photoelectric conversion layer 30d may selectively absorb light in one of infrared, red, blue, and green wavelength spectra of light. For example, the fourth photoelectric device 1200d may be an infrared/near infrared photoelectric device. In the drawing, the first electrode 10d, the photoelectric conversion layer 30d, and the second electrode 20d are sequentially stacked, but this disclosure is not limited thereto, and for example they may be stacked in an order of the second electrode 20d, the photoelectric conversion layer 30d, and the first electrode 10d.

Focusing lens (not shown) may be further formed on the fourth photoelectric device 1200d. The focusing lens may control a direction of incident light and gather the light in one region. The focusing lens may have a shape of, for example, a cylinder or a hemisphere, but is not limited thereto.

In the drawing, the first photoelectric device 1200a, the second photoelectric device 1200b, the third photoelectric device 1200c, and the fourth photoelectric device 1200d are sequentially stacked, but the present disclosure is not limited thereto, and they may be stacked in various orders.

As described above, the first photoelectric device 1200a, the second photoelectric device 1200b, the third photoelectric device 1200c, and the fourth photoelectric device 1200d have a stack structure, and thus the size of an image sensor may be reduced to realize a down-sized image sensor.

Figure 14:
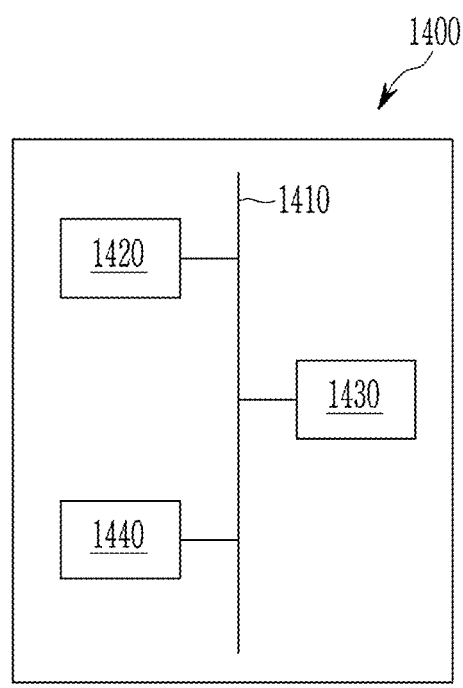
FIG. 14 is a schematic diagram of an electronic device according to some example embodiments.

FIG. 14 is a schematic diagram of an electronic device according to some example embodiments.

As shown in FIG. 14, an electronic device 1400 may include a processor 1420, a memory 1430, and an organic sensor 1440 that are electrically coupled together via a bus 1410. The organic sensor 1440 may be an organic sensor of any of the example embodiments as described herein, and the organic sensor included in the organic sensor 1440 may include any of the photoelectric devices described herein according to any of the example embodiments of the inventive concepts. The memory 1430, which may be a non-transitory computer readable medium, may store a program of instructions. The processor 1420 may execute the stored program of instructions to perform one or more functions. In some example embodiments, the processor 1420 may be configured to process electric signals generated by the organic sensor 1440. The processor 1420 may be configured to generate an output (e.g., an image to be displayed on a display interface) based on processing the electric signals.

While some example embodiments of photoelectric devices shown herein include first and second electrodes 10 and 20 facing each other and an organic layer 30 therebetween, where the organic layer may include a compound according to any of the example embodiments herein, it will be understood that in some example embodiments at least the first and second electrodes 10 and 20 may be omitted from the photoelectric device.

Hereinafter, example embodiments are illustrated in more detail with reference to examples. However, these examples are examples, and the present disclosure is not limited thereto.

Synthesis Examples

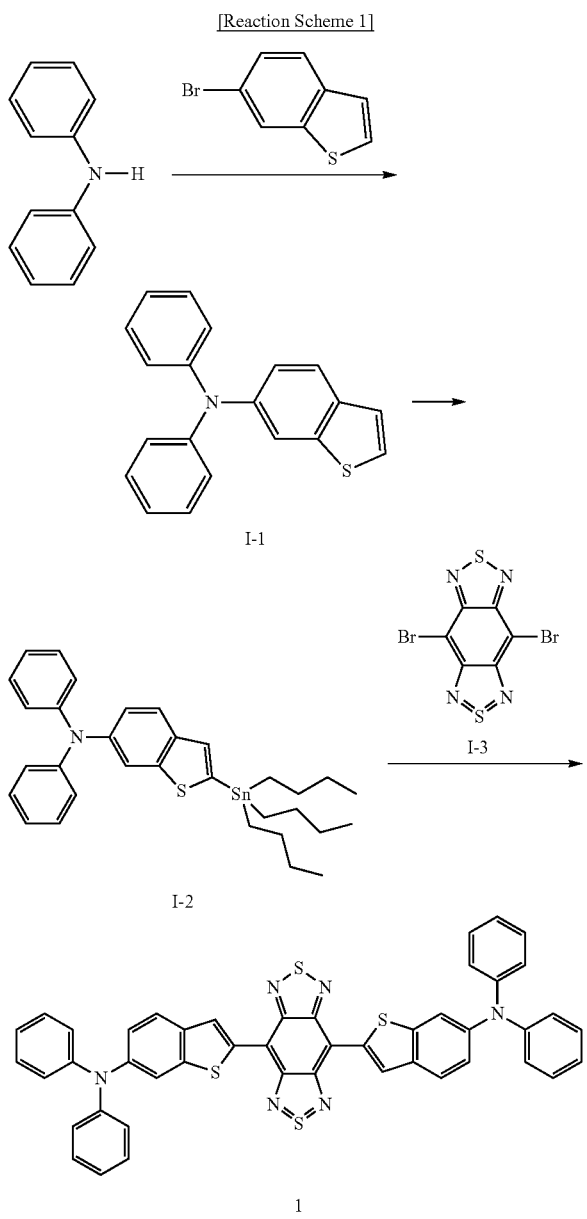

[Reaction Scheme 1]

Synthesis of Intermediate 1-1

Diphenylamine (2 g, 11.82 mmol), 6-bromobenzo[b]thiophene (2.52 g, 11.82 mmol), 5 mol % of Pd(dba)$_2$, 5 mol % of P(tBu)3, and NaOtBu (1.36 g, 14.18 mmol) are dissolved in 100 mL of toluene and then, stirred at 110° C. for 18 hours. When a reaction is complete, the toluene is concentrated, and then, 2.5 g of Intermediate 1-1 is obtained through a separation with a dichloromethane:hexane (1:1 v/v) column. Herein, a yield is 70%.

NMR (300 MHz, CDCl$_3$): 7.68 (d, 1H), 7.55 (s, 1H), 7.31 (d, 1 H), 7.28 (d, 1H), 7.22 (d, 4H), 7.15 (d, 1H), 7.10 (d, 4H), 7.01 (t, 2H).

Synthesis of Intermediate 1-2

Intermediate 1-1 (2.0 g, 6.64 mmol) is dissolved in 60 mL of THF, 2.5 M n-BuLi (2.92 mL, 7.30 mmol) is slowly added thereto at −78° C., and the obtained mixture is stirred for 4 hours. Subsequently, tributyltin chloride (2.38 g, 7.30 mmol) is slowly added thereto, and the obtained mixture is further stirred at room temperature for 4 hours. When a reaction is complete, 3.9 g of Intermediate 1-2 is obtained by an extraction using 200 mL of chloroform.

NMR (300 MHz, CDCl$_3$): 7.67 (d, 1H), 7.57 (s, 1H), 7.31 (s, 1H), 7.22 (d, 4H), 7.13 (d, 1H), 7.10 (d, 4H), 6.99 (t, 2H), 1.62 (m, 6H), 1.38 (m, 6H), 1.14 (t, 6H), 0.90 (t, 9H).

Synthesis of Compound 1

Intermediate 1-3 (0.12 g, 0.34 mmol), Intermediate 1-2 (0.44 g, 0.75 mmol), and Pd(PPh$_3$)$_4$ (0.02 g, 0.02 mmol) are dissolved in 40 mL of toluene and then, stirred at 110° C. for 18 hours. When a reaction is complete, the toluene is concentrated, and 0.1 g of Compound 1 is obtained through a separation with a dichloromethane:hexane (1:1 v/v) column and then, a precipitation in 60 mL of methanol. Herein, a yield is 36%.

LC-MS: 793.02 m/z

Evaluation I

The compound of Synthesis Example is dissolved at a concentration of 1×10$^{-5}$ M in dichloromethane to prepare a solution, and light absorption characteristics of the compound in the solution are evaluated.

In addition, the compound of Synthesis Example is sublimated under high vacuum of 10 Pa to form a 20 nm-thick thin film on a glass substrate, and light absorption characteristics of the thin film are evaluated.

The light absorption characteristics are evaluated by measuring a peak absorption wavelength (λmax) with a UV-Vis-NIR spectrometer (UV-3600 Plus, Shimadzu Corp.).

The results are shown in Table 1.

TABLE 1

|  | $\lambda_{max}$ (nm) (solution) | $\lambda_{max}$ (nm) (thin film) |
| --- | --- | --- |
| Synthesis Example 1 | 870 | 920 |

Referring to Table 1, the compound of Synthesis Example shows sufficient wavelength selectivity in a near infra-red wavelength region.

Evaluation II

Deposition characteristics of the compound of Synthesis Example are evaluated.

The deposition characteristics are evaluated by sublimating the compound under high vacuum of 10 Pa and measuring a weight loss depending on a temperature increase in a thermogravimetric analysis method.

The results are shown in Table 2.

TABLE 2

|  | $T_s$ (° C.) (−10 wt %) | $T_s$ (° C.) (−50 wt %) |
| --- | --- | --- |
| Synthesis Example 1 | 355 ± 5 | 389 ± 5 |

* $T_s$ (° C.) (−10 wt %): a temperature at which a sample exhibits a 10 wt % weight loss
* $T_s$ (° C.) (−50 wt %): a temperature at which a sample exhibits a 50 wt % weight loss Referring to Table 2, the compound of Synthesis Example has sufficient heat resistance, and accordingly, the thin film may be formed by repetitively performing a thermal evaporation.

EXAMPLES

An about 150 nm-thick anode is formed by sputtering ITO on a glass substrate. Subsequently, a 150 nm-thick photoelectric conversion layer may be formed by codepositing the compound of Synthesis Example 1 and C60 in a volume ratio of 1:1 on an anode. On the photoelectric conversion layer, an auxiliary layer is formed by depositing C60. Then, a 7 nm-thick cathode is formed on the auxiliary layer by sputtering ITO. Then, a 50 nm-thick anti-reflection layer is formed on the cathode by depositing aluminum oxide ($Al_2O_3$) and sealing it with a glass plate to manufacture a photoelectric diode.

Evaluation III

Photoelectric conversion efficiency of the photoelectric diode according to Example is evaluated.

The photoelectric conversion efficiency may be measured by using an IPCE measurement system (TNE Tech Co., Ltd., Korea). First, the IPCE measurement system is calibrated by using an Si photodiode (Hamamatsu Photonics K.K., Japan) and equipped with an organic photoelectric diode to measure external quantum efficiency in a wavelength region of about 400 nm to about 1000 nm.

The results are shown in Table 3.

TABLE 3

| | Photoelectric conversion efficiency (%) (@920 nm) |
|---|---|
| Example | 5.7 |

Referring to Table 3, the photoelectric diode according to Example shows sufficient photoelectric conversion efficiency.

While this disclosure has been described in connection with what is presently considered to be practical example embodiments, it is to be understood that the inventive concepts are not limited to the disclosed example embodiments, but, on the contrary, re intended to cover various modifications and equivalent arrangements included within the spirit and scope of the appended claims.

What is claimed is:

1. A compound represented by Chemical Formula 1:

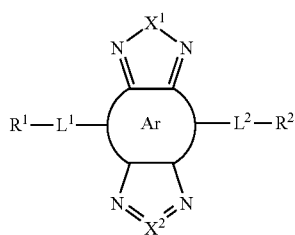

[Chemical Formula 1]

wherein, in Chemical Formula 1,
$X^1$ and $X^2$ are independently O, S, Se, Te, SO, $SO_2$, or $NR^a$,
Ar is a substituted or unsubstituted C6 to C20 aromatic ring,
$L^1$ and $L^2$ are independently one of substituted or unsubstituted groups listed in Group 1,
$R^a$ is independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and $R^1$ and $R^2$ are independently a substituted or unsubstituted amine group represented by $NR^bR^c$, wherein each $R^b$ is same or different, each $R^c$ is same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, or a halogen,

[Group 1]

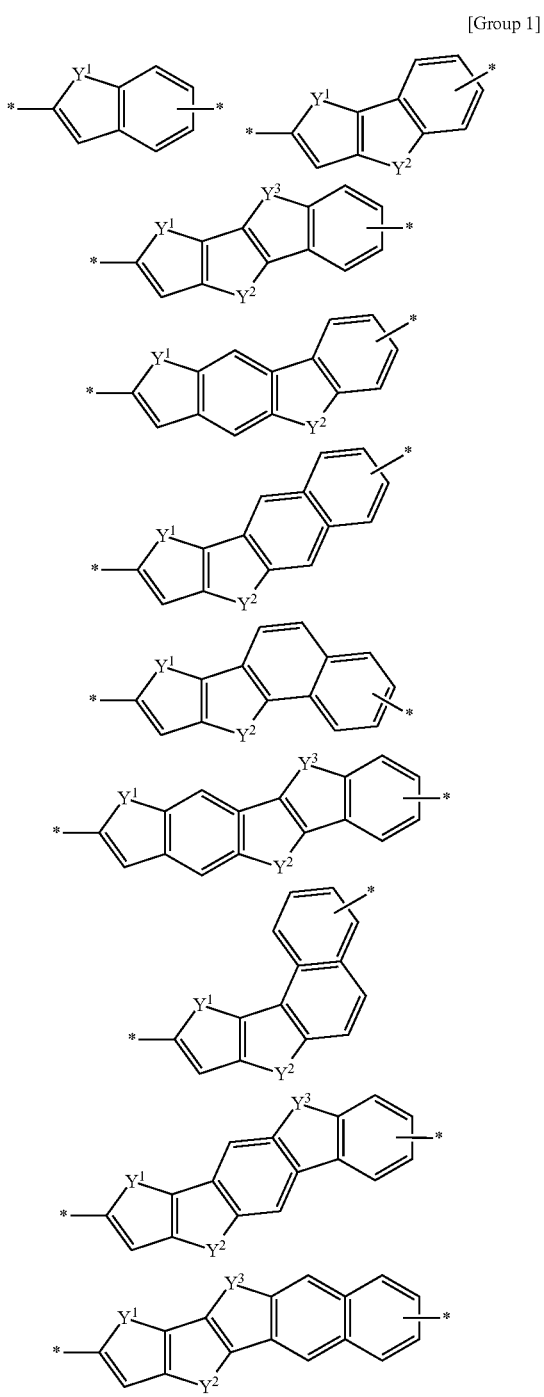

-continued

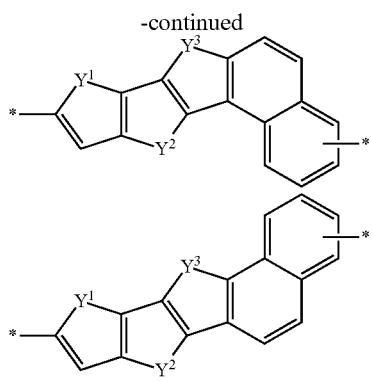

wherein, in Group 1,
Y1, Y2, and Y3 are independently O, S, Se, Te, NRd, or SiReRf,
Rd to Rf are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and
*is a linking point with Chemical Formula 1.

2. The compound of claim 1, wherein $R^1$ and $R^2$ are independently represented by one Chemical Formula of Chemical Formulae A-1 to A-3:

[Chemical Formula A-1]

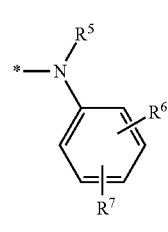

[Chemical Formula A-2]

[Chemical Formula A-3]

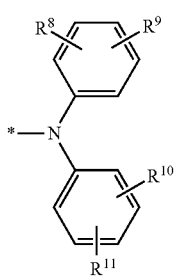

wherein, in Chemical Formulae A-1 to A-3,
$R^3$ is the same as $R^b$,
$R^4$ is the same as $R^c$,
$R^5$ is the same as $R^b$,
$R^6$ to $R^{11}$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and
*is a linking point with Chemical Formula 1.

3. The compound of claim 1, wherein the compound is represented by Chemical Formula 1B,

[Chemical Formula 1B]

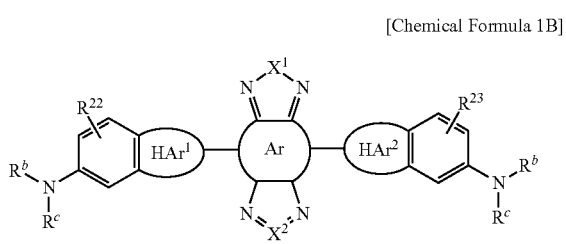

wherein, in Chemical Formula 1B,
$X^1$ and $X^2$ are independently O, S, Se, Te, SO, $SO_2$, or $NR^a$,
Ar is a substituted or unsubstituted C6 to C20 aromatic ring,
$HAr^1$ and $HAr^2$ are independently a substituted or unsubstituted thiophenylene group, a substituted or unsubstituted furanylene group, a substituted or unsubstituted selenophenylene group, a substituted or unsubstituted tellurophenylene group, or a substituted or unsubstituted pyrrolylene group,
$R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen,
each $R^b$ is the same or different,
each $R^c$ is the same or different, and
$R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, or a halogen.

4. The compound of claim 1, wherein the compound is represented by Chemical Formula 1C,

[Chemical Formula 1C]

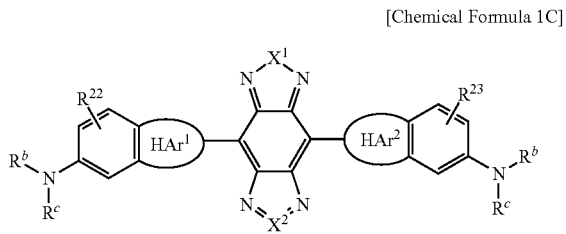

wherein, in Chemical Formula 1C,
$X^1$ and $X^2$ are independently O, S, Se, Te, SO, $SO_2$, or $NR^a$, HAr¹ and HAr² are independently a substituted or unsubstituted thiophenylene group, a substituted or unsubstituted furanylene group, a substituted or unsubstituted selenophenylene group, a substituted or unsubstituted tellurophenylene group, or a substituted or unsubstituted pyrrolylene group, $R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, each $R^b$ is the same or different, each $R^c$ is the same or different, and $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, or a halogen.

5. The compound of claim 1, wherein a peak absorption wavelength of the compound is included within a wavelength spectrum of about 750 nm to about 3000 nm.

6. A film comprising the compound of claim 1.

7. A photoelectric diode, comprising:

a first electrode and a second electrode facing each other; and an organic layer between the first electrode and the second electrode, wherein the organic layer includes a compound represented by Chemical Formula 1,

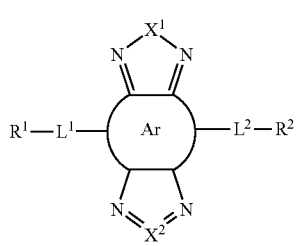

[Chemical Formula 1]

wherein, in Chemical Formula 1, $X^1$ and $X^2$ are independently O, S, Se, Te, SO, SO₂, or $NR^a$, Ar is a substituted or unsubstituted C6 to C20 aromatic ring, $L^1$ and $L^2$ are independently one of substituted or unsubstituted groups listed in Group 1, $R^a$ is independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and $R^1$ and $R^2$ are independently a substituted or unsubstituted amine group represented by $NR^bR^c$, wherein each $R^b$ is same or different, each $R^c$ is same or different, $R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, or a halogen,

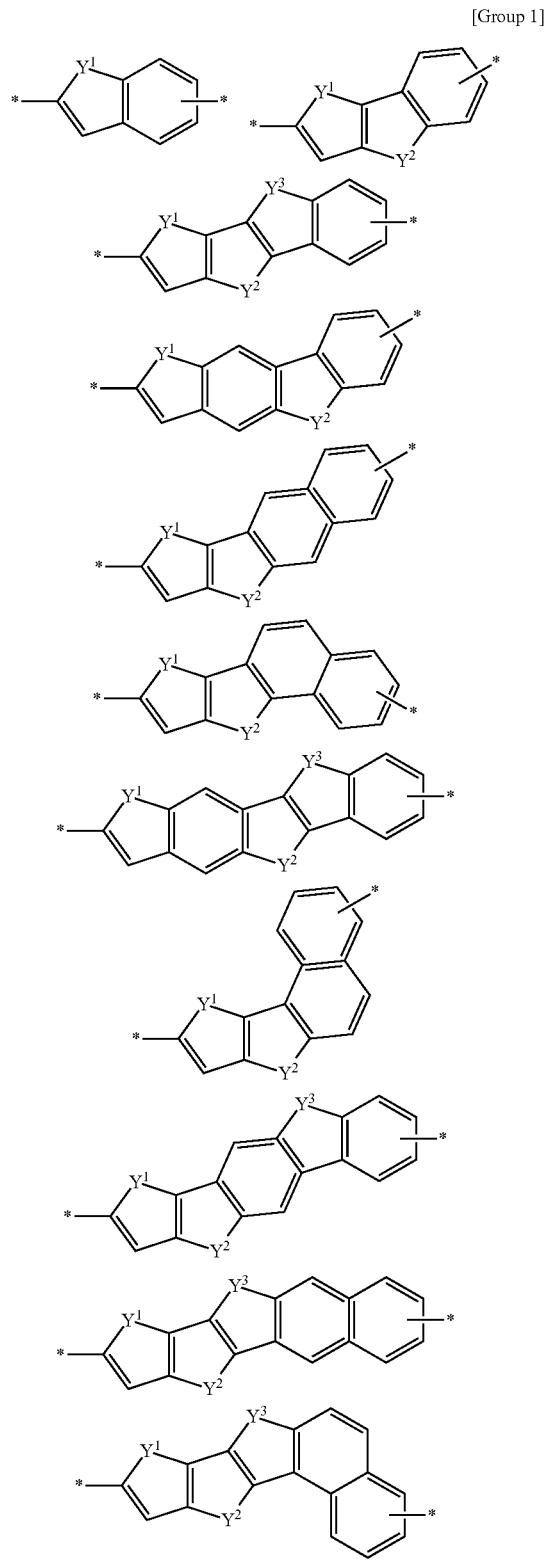

[Group 1]

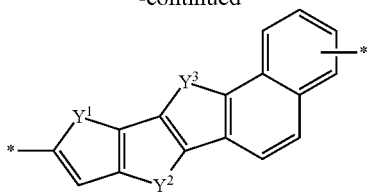

wherein, in Group 1,
Y1, Y2, and Y3 are independently O, S, Se, Te, NRd, or SiReRf,
Rd to Rf are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and
*is a linking point with Chemical Formula 1.

8. The photoelectric diode of claim 7, wherein $R^1$, $R^2$, or both $R^1$ and $R^2$ is represented by one Chemical Formula of Chemical Formulae A-1 to A-3:

[Chemical Formula A-1]

[Chemical Formula A-2]

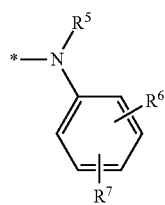

[Chemical Formula A-3]

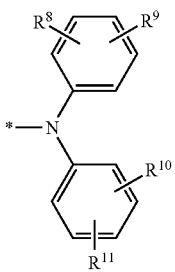

wherein, in Chemical Formulae A-1 to A-3,
$R^3$ is the same as $R^b$,
$R^4$ is the same as $R^c$,
$R^5$ is the same as $R^b$,
$R^6$ to $R^{11}$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and
*is a linking point with Chemical Formula 1.

9. The photoelectric diode of claim 7, wherein the compound is represented by Chemical Formula 1B,

[Chemical Formula 1B]

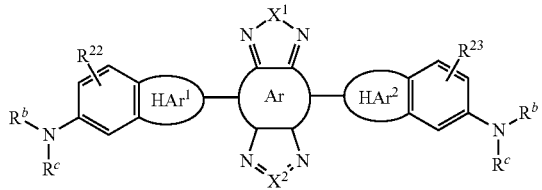

wherein, in Chemical Formula 1B,
$X^1$ and $X^2$ are independently O, S, Se, Te, SO, $SO_2$, or $NR^a$,
Ar is a substituted or unsubstituted C6 to C20 aromatic ring,
$HAr^1$ and $HAr^2$ are independently a substituted or unsubstituted thiophenylene group, a substituted or unsubstituted furanylene group, a substituted or unsubstituted selenophenylene group, a substituted or unsubstituted tellurophenylene group, or a substituted or unsubstituted pyrrolylene group,
$R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen,
each $R^b$ is the same or different,
each $R^c$ is the same or different, and
$R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, or a halogen.

10. The photoelectric diode of claim 7, wherein the compound is represented by Chemical Formula 1C,

[Chemical Formula 1C]

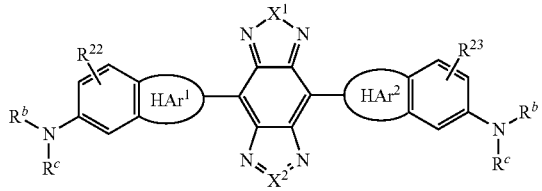

wherein, in Chemical Formula 1C,
$X^1$ and $X^2$ are independently O, S, Se, Te, SO, $SO_2$, or $NR^a$,
$HAr^1$ and $HAr^2$ are independently a substituted or unsubstituted thiophenylene group, a substituted or unsubstituted furanylene group, a substituted or unsubstituted selenophenylene group, a substituted or unsubstituted tellurophenylene group, or a substituted or unsubstituted pyrrolylene group, $R^{22}$, $R^{23}$, and $R^a$ are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen,
each $R^b$ is the same or different,
each $R^c$ is the same or different, and
$R^b$ and $R^c$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted silyl group, or a halogen.

11. The photoelectric diode of claim 7, wherein a peak absorption wavelength of the organic layer is included within to a wavelength spectrum of about 750 nm to about 3000 nm.

12. An organic sensor comprising the photoelectric diode of claim 7.

13. An electronic device comprising the organic sensor of claim 12.

14. An electronic device comprising the photoelectric diode of claim 7.

15. An organic sensor, comprising:
a semiconductor substrate; and
a photoelectric device on the semiconductor substrate, the photoelectric device configured to absorb and convert a first wavelength spectrum of incident light into electric signals, the photoelectric device including a compound represented by Chemical Formula 1,

[Chemical Formula 1]

wherein, in Chemical Formula 1,
$X^1$ and $X^2$ are independently O, S, Se, Te, SO, $SO_2$, or $NR^a$,
$A^r$ is a substituted or unsubstituted C6 to C20 aromatic ring,
$L^1$ and $L^2$ are independently one of substituted or unsubstituted groups listed in Group 1,
$R^a$ is independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, a halogen, or any combination thereof, and
$R^1$ and $R^2$ are independently a substituted or unsubstituted amine group represented by $NR^bR^c$, wherein each $R^b$ is same or different, each $R^c$ is same or different, $R^b$ and $R^c$ are independently hydrogen, a substituted or unsubstituted C 1 to C30 alkyl group, a substituted or unsubstituted C 1 to C30 alkoxy group, a substituted or unsubstituted C6 to C30 aryl group, a substituted or unsubstituted C3 to C30 heteroaryl group, a substituted or unsubstituted silyl group, or a halogen,

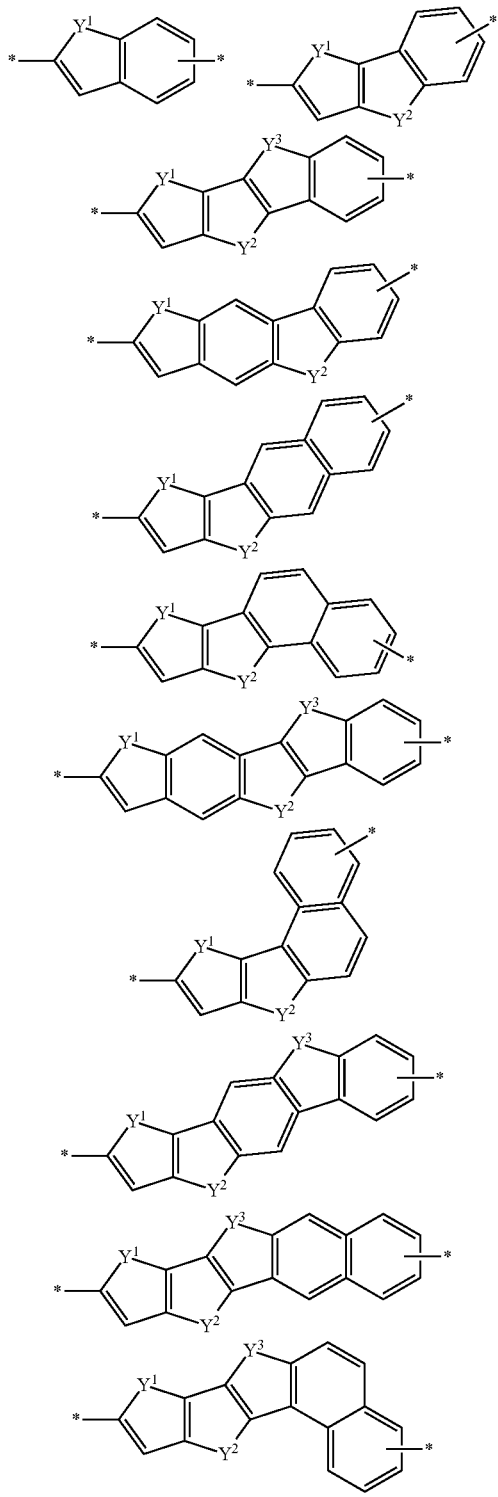

[Group 1]

-continued

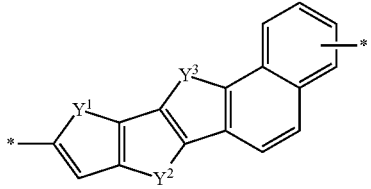

wherein, in Group 1,
Y1, Y2, and Y3 are independently O, S, Se, Te, NRd, or SiReRf,
Rd to Rf are independently hydrogen, a substituted or unsubstituted C1 to C30 alkyl group, a substituted or unsubstituted C2 to C30 alkenyl group, a substituted or unsubstituted C2 to C30 alkynyl group, a substituted or unsubstituted C1 to C30 alkoxy group, a substituted or unsubstituted C6 to C30 aryl group, a substituted or unsubstituted C3 to C30 heterocyclic group, a substituted or unsubstituted amine group, a substituted or unsubstituted silyl group, or a halogen, and
*is a linking point with Chemical Formula 1.

16. The organic sensor of claim 15, further comprising:
a plurality of photoelectric devices on the semiconductor substrate, each photoelectric device of the plurality of photoelectric devices configured to absorb and convert a different wavelength spectra of incident light into electric signals, the plurality of photoelectric devices including the photoelectric device that includes the compound represented by Chemical Formula 1.

17. The organic sensor of claim 16, wherein the plurality of photoelectric devices are stacked vertically on the semiconductor substrate, such that the plurality of photoelectric devices overlap each other in a direction extending perpendicular to a top surface of the semiconductor substrate.

18. The organic sensor of claim 17, wherein one photoelectric device of the plurality of photoelectric devices overlaps with a limited portion of another photoelectric device of the plurality of photoelectric devices in the direction extending perpendicular to the top surface of the semiconductor substrate.

19. The organic sensor of claim 16, wherein the plurality of photoelectric devices are arranged horizontally on the semiconductor substrate, such that the plurality of photoelectric devices overlap each other in a direction extending parallel to a top surface of the semiconductor substrate.

20. The organic sensor of claim 15, wherein the first wavelength spectrum of incident light includes an infrared or near-infrared wavelength spectrum of incident light.

21. The organic sensor of claim 15, further comprising:
a photo-sensing device integrated in the semiconductor substrate, the photo-sensing device configured to convert a second wavelength spectrum of incident light into electric signals.

22. The organic sensor of claim 21, further comprising:
a color filter configured to selectively transmit a particular wavelength spectrum of incident light to the photo-sensing device, the particular wavelength spectrum of incident light including at least the second wavelength spectrum of incident light, such that the photo-sensing device is configured to absorb the second wavelength spectrum of incident light.

23. The organic sensor of claim 22, wherein the photoelectric device is between the color filter and the photo-sensing device.

24. The organic sensor of claim 22, wherein the photo-sensing device is between the color filter and the photoelectric device.

25. An electronic device comprising the organic sensor of claim 15.

* * * * *